(12) United States Patent
Wang et al.

(10) Patent No.: US 12,377,095 B2
(45) Date of Patent: *Aug. 5, 2025

(54) USE OF LIGUSTRAZINE NITRONE DERIVATIVES IN TREATMENT AND PREVENTION OF DIABETIC COMPLICATION DISEASES

(71) Applicant: QINGDAO HAILAN PHARMACEUTICALS CO., LTD., Qingdao (CN)

(72) Inventors: Yuqiang Wang, Qingdao (CN); Yewei Sun, Qingdao (CN); Lipeng Xu, Qingdao (CN); Mei Jing, Qingdao (CN); Zaijun Zhang, Qingdao (CN); Gaoxiao Zhang, Qingdao (CN); Pei Yu, Qingdao (CN); Peng Yi, Qingdao (CN)

(*) Notice: Subject to any disclaimer, the term of this patent is extended or adjusted under 35 U.S.C. 154(b) by 897 days.

This patent is subject to a terminal disclaimer.

(21) Appl. No.: 17/300,777

(22) Filed: Nov. 3, 2021

(65) Prior Publication Data
US 2022/0202812 A1 Jun. 30, 2022

Related U.S. Application Data

(63) Continuation-in-part of application No. 16/602,714, filed on Nov. 22, 2019, now Pat. No. 11,197,855.

(51) Int. Cl.
*A61K 31/4965* (2006.01)
*A61P 3/10* (2006.01)

(52) U.S. Cl.
CPC ............ *A61K 31/4965* (2013.01); *A61P 3/10* (2018.01)

(58) Field of Classification Search
CPC .............................. A61K 31/4965; A61P 3/10
USPC ...................................................... 514/252.1
See application file for complete search history.

(56) References Cited

U.S. PATENT DOCUMENTS 11,197,855 B2 * 12/2021 Wang .................. A61P 3/10

OTHER PUBLICATIONS

Mohanram et al, Anemia and end-stage renal disease in patients with type 2 diabetes and nephropathy, Kidney International, vol. 66 (2004), pp. 1131-1138 (Year: 2004).*

* cited by examiner

*Primary Examiner* — Taylor V Oh
(74) *Attorney, Agent, or Firm* — Panterrain IP Law; Charles Liu

(57) ABSTRACT

The present invention relates to the use of ligustrazine nitrone derivatives and pharmaceutical composition thereof for the treatment and prevention of diseases of diabetic complications, which include renal anemia. The ligustrazine nitrone derivatives have the structure of the general formula (I).

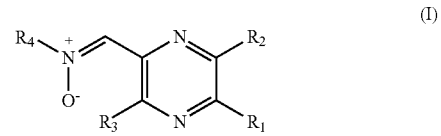

Experimental results indicated that the ligustrazine nitrone derivatives can significantly increase the levels of serum iron and erythropoietin in STZ induced SD rats and spontaneously hypertensive rats, and can be used for treating and preventing renal anemia caused by decrease in renal EPO production and/or concomitant iron deficiency. Therefore, the ligustrazine nitrone derivatives can be made into various dosage forms with a drug carrier. The derivatives can be prepared into various dose forms together with drug carriers.

19 Claims, 10 Drawing Sheets

Table 1. Number of occurrences and time of appearance of retinopathy in diabetic nephropathy model rats
| Group | Retinopathy Number of cases | Time of Retinopathy (nth day from the date of successful modeling) | | | | | | |
|---|---|---|---|---|---|---|---|---|
| | | #1 | #2 | #3 | #4 | #5 | #6 | #7 |
| Control | 0 | / | / | / | / | / | / | / |
| Model | 6 | 27 | 28 | 33 | 36 | 37 | 37 | / |
| TBN (10 mg/kg) | 3 | 23 | 24 | 28 | / | / | / | / |
| TBN (30 mg/kg) | 6 | 36 | 39 | 40 | 40 | 41 | 41 | / |
| TBN (60 mg/kg) | 2 | 39 | 42 | / | / | / | / | / |
| TN-2 (30 mg/kg) | 3 | 24 | 38 | 42 | / | / | / | / |
| Losartan(10 mg/kg) | 3 | 36 | 36 | 39 | / | / | / | / |
| TBN (60 mg/kg) + Losa.(10 mg/kg) | 6 | 31 | 32 | 33 | 36 | 36 | 38 | / |
FIG. 5
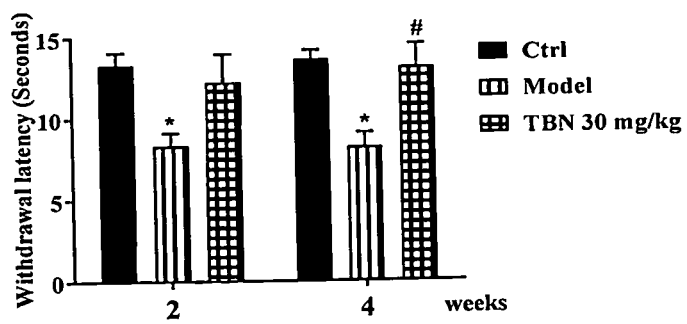
FIG. 6
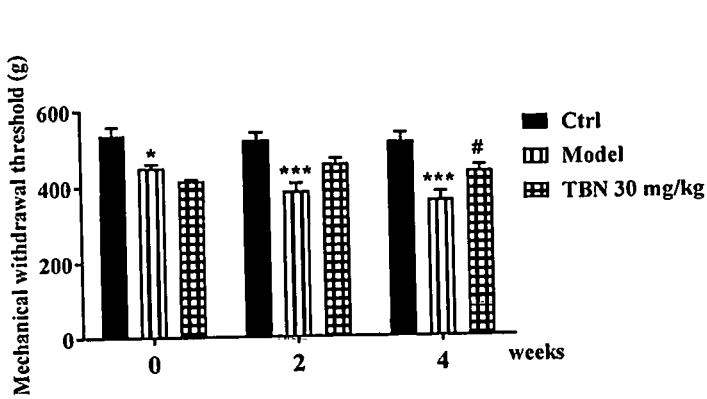
FIG. 7
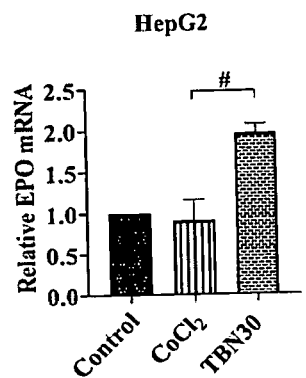
FIG. 8

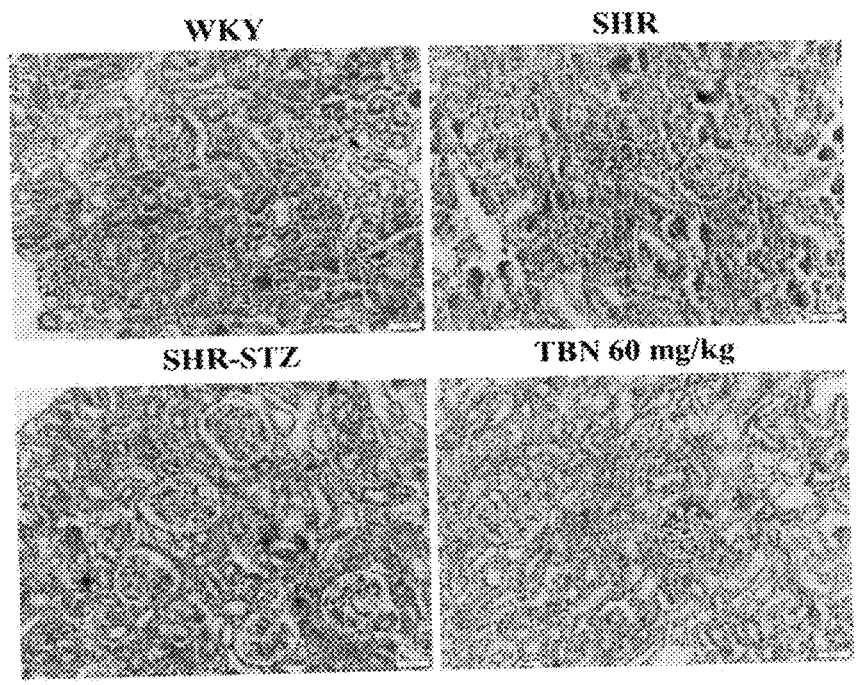
FIG. 20
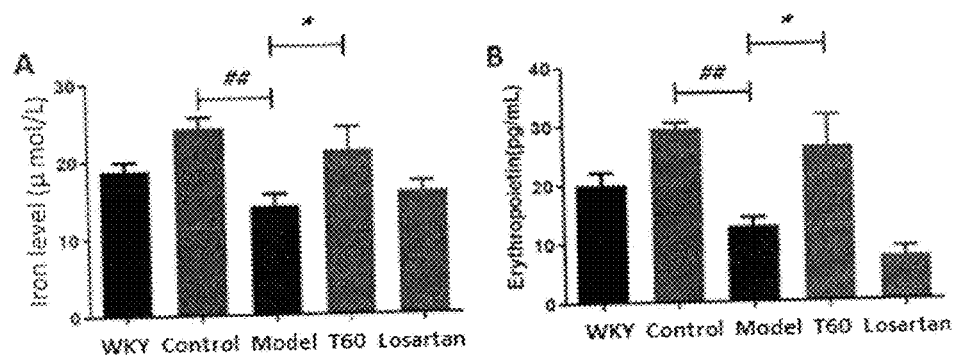
FIG. 21
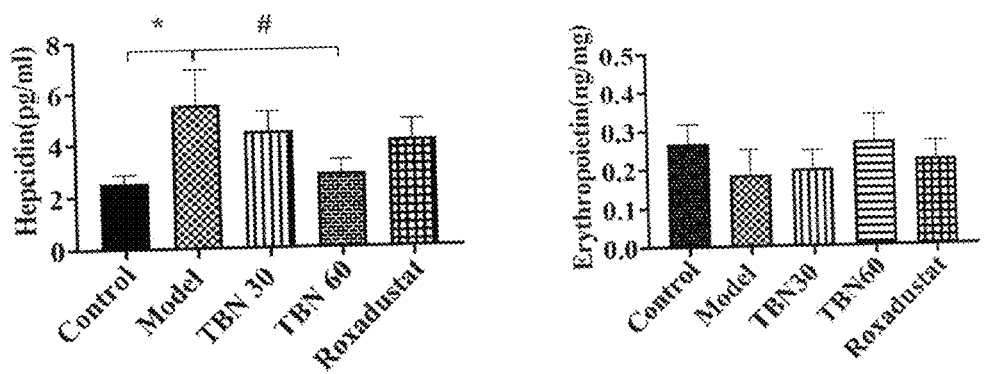
FIG. 22
FIG. 23

USE OF LIGUSTRAZINE NITRONE DERIVATIVES IN TREATMENT AND PREVENTION OF DIABETIC COMPLICATION DISEASES

FIELD OF THE INVENTION

The present invention relates generally to the field of medicine and, more particularly, to the use of ligustrazine nitrone derivatives and pharmaceutical composition thereof in the treatment and prevention of the disease of renal anemia.

BACKGROUND OF THE INVENTION

Diabetes are metabolic diseases characterized by hyperglycemia due to defects in insulin secretion or impaired insulin action. Sustained hyperglycemia and long-term metabolic disorders can cause damages or even dysfunction and failure to the systemic tissues and organs, especially eyes, kidneys, cardiovascular and nervous system, and in severe cases, can cause complications of ketoacidosis, such as electrolyte imbalance and acid-base balance disorders, and hyperosmolar coma dehydration.

Diabetic Kidney Disease (DKD) is one of the most important microvascular complications with clinical features of proteinuria, progressive renal impairment, hypertension, edema, and severe renal failure in the late stage. DKD is currently the leading cause of end-stage renal disease, with approximately 30% to 40% of diabetic patients suffering from kidney disease. According to IDF, the global prevalence of diabetes in 2013 was 382 million, and may grow to 592 million in 25 years.

So far, the mechanism for the development of DKD has not been fully clarified. However, it is currently believed that the pathogenesis of DKD is related to the disorder of glucose metabolism and the resulting non-enzymatic glycation, activation of the polyol pathway, activation of protein kinase C, disorders of lipid metabolism, renal hemodynamic changes caused by hypertension, and oxidation stimulation, vasoactive substances and cytokines, genetics. It is reported that mitochondria are the main source of intracellular reactive oxygen species (ROS) and an important participant in the endogenous apoptotic pathway. The excessive synthesis of ROS may be the starting point in the pathogenesis of diabetes and its complications, and blocking or clearance of ROS can reduce the increase in urinary protein excretion, glomerular sclerosis, and tubulointerstitial fibrosis caused by diabetic nephropathy (Michael Brownlee, Nature, 2001, 414: 813-820).

Diabetic eye disease is also one of the common complications of diabetes. During the course of diabetes, most of the tissues of the eyes of the patient of diabetes are affected, resulting in ocular lesions of varying degrees and different symptoms. Eye diseases caused by diabetes mainly include retinopathy, cataracts and glaucoma.

Ligustrazine (Tetramethylpyrazine) is one of the main active ingredients of traditional Chinese medicine Chuanxiong (*Ligusticum wallichii*). It is widely used in the treatment of diseases such as cardio-cerebral vascular disease, nephropathy, retinopathy, and optic nerve ischemic eye disease. Previous studies have confirmed that ligustrazine has pharmacological activities including anti-thrombosis, anti-ischemic reperfusion, protection of cardio-cerebral vascular system, liver, and kidney (Modern Chinese Medicine in China, 2016, 18 (10): 1364-1370). The structure of tetramethylpyrazine is as follows:

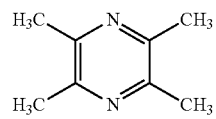

Tetramethylpyrazine can exert renal cell cytoprotection through anti-apoptosis, anti-inflammatory, anti-oxidation and other ways, thereby reducing functional damage of the kidney. Yang et al (Phytomedicine, 2011, 18 (13): 1148-1152), in their studies of rat diabetic nephropathy induced by streptozotocin, showed that tetramethylpyrazine can significantly improve renal function and down-regulate blood glucose and urine protein exclusion in rats with diabetic nephropathy. The mechanism of action may be related to the down-regulation of VEGF in kidney tissue by tetramethylpyrazine. Gong et al (Archives of Toxicology, 2015, 89 (7): 1057-1070) demonstrated that tetramethylpyrazine also has protective activity against sodium arsenite-induced damage to human renal proximal tubule cells, and its mechanism is related to inhibition of ROS production, increase in GSH level, increase of cytochrome C oxidase activity, restoration of mitochondrial membrane potential, improvement of mitochondrial dysfunction and reduction of protein expression of β-catenin, NF-κB, p38 MAPK, TNF-α, COX-2, thereby blocking cell apoptosis. At the same time, Gong et al also confirmed in their other studies on tetramethylpyrazine (Am J Nephrol, 2013, 37 (3): 199-207) that tetramethylpyrazine may be protective in kidney damage model induced by contrast agent through inhibition of p38 MAPK protein expression.

Clinical studies have shown that tetramethylpyrazine has certain therapeutic effect on diabetic nephropathy and has high safety. Yang Lin et al (Chinese Journal of Information on TCM, 2011, 18 (8): 26-29) systematically evaluated the clinical study of tetramethylpyrazine injection in the treatment of diabetic nephropathy, and the results showed that, the combined application of tetramethylpyrazine, as compared with the conventional treatment group, can reduce 24 h urinary albumin excretion rate, 24 h total urine proteins and 24 h urine protein quantitation in patients with diabetic nephropathy, but its effect on reduction of blood urea nitrogen, diastolic blood pressure and systolic blood pressure is not significant. At the same time, there was no indication of serious adverse reaction during the use, which suggests that tetramethylpyrazine injection has certain curative effect on patients with diabetic nephropathy. Chen Yingjun et al (China Practical Medicine, 2013, 8 (23): 178-179) found that, in the treatment of patients with type 2 diabetes with peripheral neuropathy, large doses of tetramethylpyrazine injection (360-400 mg/d) via intravenous drops with 12 d as one course of treatment, the total effective rate of treatment is as high as 95%, while the conventional dose of tetramethylpyrazine injection group (80 mg/d) is 82.93%. The total effective rate of the high dose group is higher than that of the conventional dose group, without increase of tadverse reactions.

Tetramethylpyrazine is also widely used in the treatment of ophthalmic diseases. At present, tetramethylpyrazine is clinically applied to treat eye diseases, such as diabetic retinopathy, retinal vascular occlusion, ischemic retinopathy, and glaucoma. Deng Xinguo et al used intraperitoneal injection of tetramethylpyrazine hydrochloride to observe the pharmacokinetics of retinal tissue in rabbit eyes, and their study showed that after intraperitoneal injection of tetramethylpyrazine, the drug can enter the retinal tissue through the blood-retinal barrier. This result provides an experimental basis for the treatment of fundus diseases by systemic administration of tetramethylpyrazine. Some researchers divided 40 patients with diabetic retinopathy into 20 patients in the treatment group and 20 patients in the control group. In the treatment group, the patients were intravenously instilled with puerarin injection, and took orally traditional Chinese medicine of Zishen Jianpi Huayu Recipe, and applied with electronically controlled tetramethylpyrazine ion. In the control group, the patients were intravenously instilled with puerarin injection, and took orally traditional Chinese medicine of Zishen Jianpi Huayu Recipe. The changes of the two groups before and after treatment and the fundus were observed. The results showed that the total effective rate was 86.84% in the treatment group and 67.50% in the control group. The therapeutic effect of the treatment group was significantly better than that of the control group. The difference between the two groups was statistically significant (Wang Yan, Chinese Journal of Ophthalmology, 2004). The mechanism of action of tetramethylpyrazine in the treatment of fundus diseases is generally considered to be related to improving blood rheology, inhibiting cell proliferation, scavenging free radicals, inhibiting apoptosis and antagonizing calcium ions.

In summary, tetramethylpyrazine may alleviate diabetic nephropathy and fundus diseases through anti-apoptosis, anti-inflammatory and anti-oxidation, and shows some therapeutic effects on diabetic nephropathy in clinical research, but its free radicals scavenging ability is insufficient, and thus the treatment effect of it cannot meet the clinical needs.

Renal anemia refers to anemia caused by the relative or absolute deficiency of erythropoietin (EPO) caused by various kidney diseases, and anemia caused by some toxic substances in the plasma of uremia patients through interference with the production and metabolism of red blood cells.

The reduction of EPO synthesis and the resulting disorder of hematopoietic stem cell synthesis are the main causes of renal anemia. EPO is a hematopoietic cytokine mainly produced by the renal cortex, and the secondary source is the liver. After synthesis, it is directly secreted into the blood, but is not stored in the cells it produces, and the volume of its distribution in the circulation is close to the volume of plasma. When the renal cortex is damaged, EPO production is reduced; blocking the mature differentiation of progenitor cells into red blood cells and reticulocytes, and the survival rate of immature red blood cells is reduced, leading to anemia. Under normal physiological conditions, about 90% of EPO is produced by the kidney; when the body tissue is hypoxic, the level of erythropoietin in the blood increases, which stimulates increased bone marrow erythropoiesis, and the secretion of erythropoietin is also affected by the negative feedback regulation of decrease in the number of red blood cells. In the pathological state of diabetic nephropathy, high glucose induces renal tubular interstitial damage and insufficient EPO synthesis, which in turn leads to the occurrence of anemia. In addition, the decrease in EPO synthesis even precedes the decrease in glomerular filtration rate (eGFR) and the appearance of proteinuria.

Another cause of renal anemia is iron deficiency. Iron deficiency is common in patients with chronic kidney disease. The incidence of iron deficiency in non-dialysis patients with chronic kidney disease is higher than 50%, and the proportion of patients receiving dialysis is even higher. The lack of iron in erythropoiesis in patients with chronic kidney disease is often accompanied by relative blockade of intestinal iron absorption and decreased release of stored iron in macrophages and liver. This iron block is mainly mediated by the hepcidin produced by the liver. The increased concentration of hepcidin leads to the internalization of iron transporter into the cell. As a result, iron does not enter the circulation through intestinal cells or storage tissues. The concentration of hepcidin is related to the body's iron storage, inflammation, anemia, and EPO levels. In the pathological state of chronic kidney disease, inflammation stimulates hepcidin to maintain a high level, blocking the iron required to produce red blood cells.

Nitrone derivatives are a class of compounds with strong free radical scavenging ability with strong scavenging effects on various active free radicals. It is found that nitrone derivatives have certain therapeutic effects on various diseases induced by free radicals, such as cancer, stroke, and Parkinson's disease. Based on the clinical application of tetramethylpyrazine in the treatment of diabetic nephropathy and fundus diseases, and the strong free radical scavenging effect of nitrone compounds, we have creatively synthesized ligustrazine nitrone derivatives TBN and TN-2. Studies have found that the ligustrazine nitrone derivatives have a significant protective effect on diabetic nephropathy rat model, and can significantly reduce blood glucose, reduce serum creatinine, reduce urea nitrogen levels and urine protein levels, and reduce kidney index in STZ-induced diabetic nephropathy model rats. At the same time, the ligustrazine nitrone derivatives can significantly reduce the incidence of diabetic retinopathy.

In the present invention, a new use of the ligustrazine nitrone derivatives has been found in the manufacture of medicaments for the prevention and treatment of a disease of diabetic complications. The compounds TBN and TN-2 of the present invention are provided by coupling of the derivatives of tetramethylpyrazine and nitrone groups, and the compounds have both the activities of anti-oxidation, anti-apoptosis, and anti-inflammatory of the derivatives of tetramethylpyrazine, and the strong radical scavenging activity of nitrone groups. While the efficacy of ligustrazine on diabetic nephropathy is retained, the therapeutic effects on hyperglycemia or free radical-induced oxidative damage have been improved. On the other hand, TBN and TN-2 have also shown certain therapeutic effects on diabetic retinopathy, and can delay the progression of diabetic nephropathy and diabetic retinopathy, to bring higher benefits to the patients.

The ligustrazine nitrone derivatives TBN and TN-2 of the present invention can be used in combination with the clinically available drugs in the treatment of diabetes and diabetic nephropathy, to synergistically improve the therapeutic effect, reduce the side effects of existing clinical drugs, and improve the benefit/risk ratio of the clinical drugs.

SUMMARY OF THE INVENTION

The present invention provided a new use of ligustrazine nitrone derivatives and pharmaceutical compositions thereof, namely, use of nitrone derivatives of tetramethylpyrazine in the treatment and prevention of a disease of diabetic complications. The derivatives have the structure of the following formula (I):

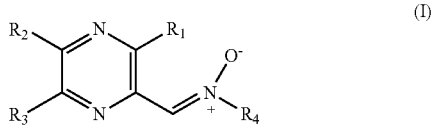

(I)

Wherein $R_1$ and $R_3$ are each independently C1-C6 alkyl; $R_2$ is C1-C6 alkyl or

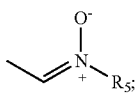

and $R_4$ and $R_5$ are each independently sec-butyl, isobutyl, t-butyl, cyclopentyl or cyclohexyl.

Preferably, the C1-C6 alkyl is methyl, ethyl, n-propyl, isopropyl, n-butyl, isobutyl, tert-butyl or n-pentyl.

Further preferably, the ligustrazine nitrone derivatives have a structure of the following formula:

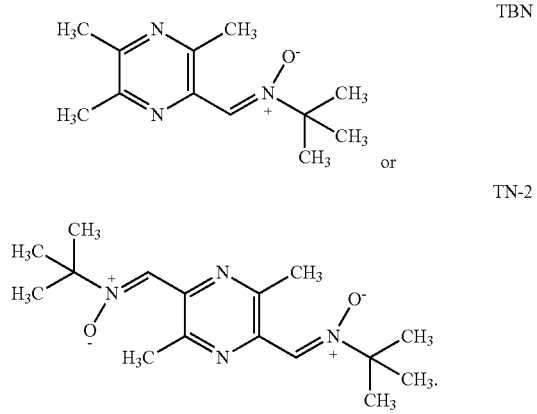

The present invention provides the use of the ligustrazine nitrone derivatives and pharmaceutical compositions thereof for the treatment and prevention of the diseases of diabetic complications.

In some embodiments, the disease of diabetic complications includes diabetic eye disease, kidney disease, or neuropathy.

In some embodiments, the disease of diabetic complications is diabetic nephropathy and diabetic ophthalmopathy. For example, the diabetic ophthalmopathy is retinopathy, glaucoma and cataract.

In other embodiments, the disease of diabetic complications is renal anemia.

The present invention provided use of the ligustrazine nitrone compound or its pharmaceutically acceptable salt in the prevention and/or treatment of renal anemia, and the use of the ligustrazine nitrone compound or its pharmaceutically acceptable salt in the preparation of a medicine for the prevention and/or treatment of renal anemia. The renal anemia refers to anemia caused by reduced EPO production and/or concomitant iron deficiency when renal function declines due to various kidney diseases.

In some embodiments, the renal anemia includes but is not limited to diabetic nephropathy renal anemia, chronic kidney disease (CKD) complicated renal anemia, cancer complicated renal anemia, and the like. The cancer complicated renal anemia in the present invention includes renal anemia caused by cancer radiotherapy or chemotherapy.

In some embodiments of the present application, the diabetic nephropathy renal anemia includes nephropathy renal anemia caused by Type 1 diabetes or Type 2 diabetes The present invention also provides the use of the ligustrazine nitrone derivatives and a pharmaceutical composition thereof for manufacturing a medicament, wherein the medicament can be used for preventing and treating diabetic nephropathy and its compositions. The pharmaceutical composition comprises a therapeutically effective amount of the ligustrazine nitrone derivative or a pharmaceutically acceptable salt thereof, and a pharmaceutically acceptable carrier.

The medicament containing the ligustrazine nitrone derivatives may be used alone or in combination with other drugs for preventing and treating a disease of diabetic complications. The other drugs that can be used in combination are mainly oral antidiabetic drugs commonly used in clinical practice, including biguanides, sulfonylureas, glucosidase inhibitors, thiazolidinediones, non-sulfonylureas, and dipeptidyl peptidases inhibitors. Preferred drugs in the combination are angiotensin receptor blockers, angiotensin converting enzyme inhibitors and folic acid. Studies have shown that folic acid protects diabetic nephropathy by lowering homocysteine.

The ligustrazine nitrone derivatives can be formulated into various dosage forms with a pharmaceutical carrier, including tablets, granules, injections, powders, capsules, and suspensions.

Preferably, the therapeutically effective amount of the ligustrazine nitrone derivatives is from 0.001 to 2 g/kg body weight.

As used herein, "combined use" means that two or more active substances can be administered to a subject together as a mixture, simultaneously as separate formulations, or sequentially in any order as separate formulations. For example, the ligustrazine nitrone compound of the present invention is used in combination with other drugs, which are for the prevention and treatment of diabetic nephropathy, chronic kidney disease or cancer, in the prevention and treatment of diabetic nephropathy complicated renal anemia, chronic kidney disease complicated renal anemia or cancer complicated renal anemia.

The ligustrazine nitrone compound of the present invention or its pharmaceutically acceptable salt is used in combination with blood pressure lowering drugs, such as angiotensin-converting enzyme inhibitors (e.g., Angiotensin-Converting Enzyme Inhibitors, ACEI), angiotensin II receptor antagonists (e.g., Angiotensin II Receptor Antagonist, ARB), calcium channel blockers, β-receptor blockers, and diuretics, for the prevention and treatment of hypertension with renal anemia. The ligustrazine nitrone compound or its pharmaceutically acceptable salts is used in combination with blood glucose regulating drugs, such as biguanides, sulfonylureas, glinides, α-glucosidase inhibitors, thiazolidinediones, dipeptidyl peptidase (DPP-4) inhibitors, and insulin, for the prevention and treatment of diabetes mellitus complicated renal anemia. The ligustrazine nitrone compound or its pharmaceutically acceptable salt is used in combination with a hypoxia-inducible factor proline hydroxylase (HIF-PH) inhibitor for the prevention or treatment of renal anemia.

The ligustrazine nitrone compound or its pharmaceutically acceptable salt is used in combination with losartan in a medicine for preventing and treating hypertension complicated renal anemia; the ligustrazine nitrone compound or its acceptable salt is used in combination with metformin in medicines for the prevention and treatment of diabetes renal anemia; the ligustrazine nitrone compound or its pharmaceutically acceptable salt is used in combination with roxadustat for prevention and treatment of renal anemia.

The present invention provides also a method for the treatment of renal anemia, which comprises administering to a patient a pharmaceutical composition of the ligustrazine nitrone compound or its pharmaceutically acceptable salt. The method can also include administering to a patient the ligustrazine nitrone compound or its pharmaceutically acceptable salt with other active substances.

The use of the ligustrazine nitrone compound or its pharmaceutically acceptable salt for the prevention and/or treatment of renal anemia can effectively increase the production of renal EPO and the content of iron ions, and can be used for the prevention and/or treatment of the renal anemia caused by reduced EPO production and/or concomitant iron deficiency when renal function declines due to various kidney diseases.

The ligustrazine nitrone compound of the present invention has activities including both ligustrazine anti-oxidation, anti-apoptosis, anti-inflammatory activities, and strong free radical scavenging activity with the nitrone group, and while retaining the therapeutic effect of ligustrazine on DKD, it can improve the oxidative damage of renal cortex induced by hyperglycemia or free radicals, and at the same time, it can also prevent and/or treat renal anemia. In the STZ-induced DKD model of SD rats, the db/db mouse spontaneous diabetes model, and the STZ-induced SHR rat model of diabetes with hypertension, the ligustrazine nitrone compounds of the present invention, as compared with losartan, shows excellent therapeutic effects on diabetic nephropathy. Different from the existing diabetes treatment drugs ACEI and ARB, which have adverse reactions leading to reduction of serum erythropoietin, the ligustrazine nitrone compound of the present invention, in the STZ-induced DKD model of SD rats, STZ-induced diabetic model with hypertension of SHR rats and spontaneous diabetic model in rhesus monkeys, TBN can increase the serum EPO and iron content, while the reduction of EPO and iron ions are the predisposing factors for renal anemia, and thus, TBN can reduce the incidence of diabetic complications and renal anemia.

The ligustrazine nitrone compound or its pharmaceutically acceptable salt of the present invention can also be used in combination with clinically existing therapeutic drugs for the treatment of diabetes and diabetic nephropathy, which improves the curative effect through synergy, reduces the side effects of existing clinical drugs, and improves clinical drug benefit/risk ratio.

BRIEF DESCRIPTION OF THE DRAWINGS

FIG. 5 shows Table 1 which lists the number of occurrences and time of appearance of retinopathy in diabetic nephropathy model rats.

FIG. 6 shows the test results of mechanical pain threshold in diabetic neuropathy model rats. Values were shown as the means±SEM. n=7 for each group. ***$P<0.001$ vs control group, #$P<0.05$ vs rats treated with STZ alone group after 8 weeks.

FIG. 7 shows the experimental results of thermal radiation stimulation in diabetic neuropathy model rats. Values were shown as the means±SEM. n=7 for each group. *$P<0.05$ vs control group, #$P<0.05$ vs rats treated with STZ alone group after 8 weeks.

FIG. 8 shows the expression results of EPO mRNA levels in cells in a cellular hypoxia model.

FIG. 20 shows the effect of TBN on the glomerular index of SHR rats induced by STZ. Wherein, WKY group: n=16; SHR group: n=16; SHR-STZ group: n=16; SHR-STZ+TBN group: n=16; SHR-STZ+Losartan group: n=16.

FIG. 21 shows the effect of TBN on iron ions and EPO in the serum of STZ-induced SHR rats. Wherein, WKY group: n=16; SHR group: n=16; SHR-STZ group: n=16; SHR-STZ+TBN group: n=16; SHR-STZ+Losartan group: n=16 only.

FIG. 22 shows the effect of TBN on the level of hepcidin in mice; where *$P<0.05$ vs. Model mice; #$P<0.05$ vs. Control mice. Wherein, control group: n=8; model group: n=7; TBN 30 mg/kg group: n=8; TBN 60 mg/kg group: n=7; Roxadustat 10 mg/kg group: n=8.

FIG. 23 shows the effect of TBN on the level of hepcidin in mice; where *$P<0.05$ vs. Model mice; #$P<0.05$ vs. Control mice. Wherein, control group: n=8; model group: n=7; TBN 30 mg/kg group: n=8; TBN 60 mg/kg group: n=7; Roxadustat 10 mg/kg group: n=8.

DETAILED DESCRIPTION OF EMBODIMENTS

Some specific embodiments or examples of the present invention will be described below. It will be understood that these specific embodiments or examples are only used for further explanation of the invention, rather than to limit the scope of the inventive subject matters as defined by the claims.

Example 1. Preparation and Grouping of STZ-Induced Diabetic Nephropathy Rat Model 1. Model Making SD rats (200±10 g) were used as model animals, which were fasted for 12 h before injection. STZ was dissolved in citrate buffer at 1% concentration, and rats were fasted and intraperitoneally injected with 55 mg/kg STZ and placed in the cage, the rats being ensured with adequate water intake for 24 h. STZ injections need to be fast and complete within 10 minutes of injection. The normal control group was injected with an equal volume of pH 4.5 citric acid-sodium citrate buffer. The state of the animals (multiple drinking and polyuria) was observed. After 3 weeks of STZ injection, blood was collected from the tail vein, and fasting blood glucose ≥16.7 mmol/L was measured as the standard for diabetic nephropathy in rats.

2. Grouping

DKD rats were randomly assigned to 6 groups and given with different drugs. After 6 weeks of administration, the experiment was terminated and the protective effect of the drug on DKD rats was observed.

Example 2. Effect of 1 Ligustrazine Nitrone Derivatives on Body Weight, Food Intake and Water Intake of STZ-Induced DKD Rats The general condition and body weight changes after rat modeling were observed weekly. The general conditions include the activity, mental state, coat color, diet, water intake and urine volume of the rats. The amount of water and the amount of feed were recorded weekly.

Figure 1:
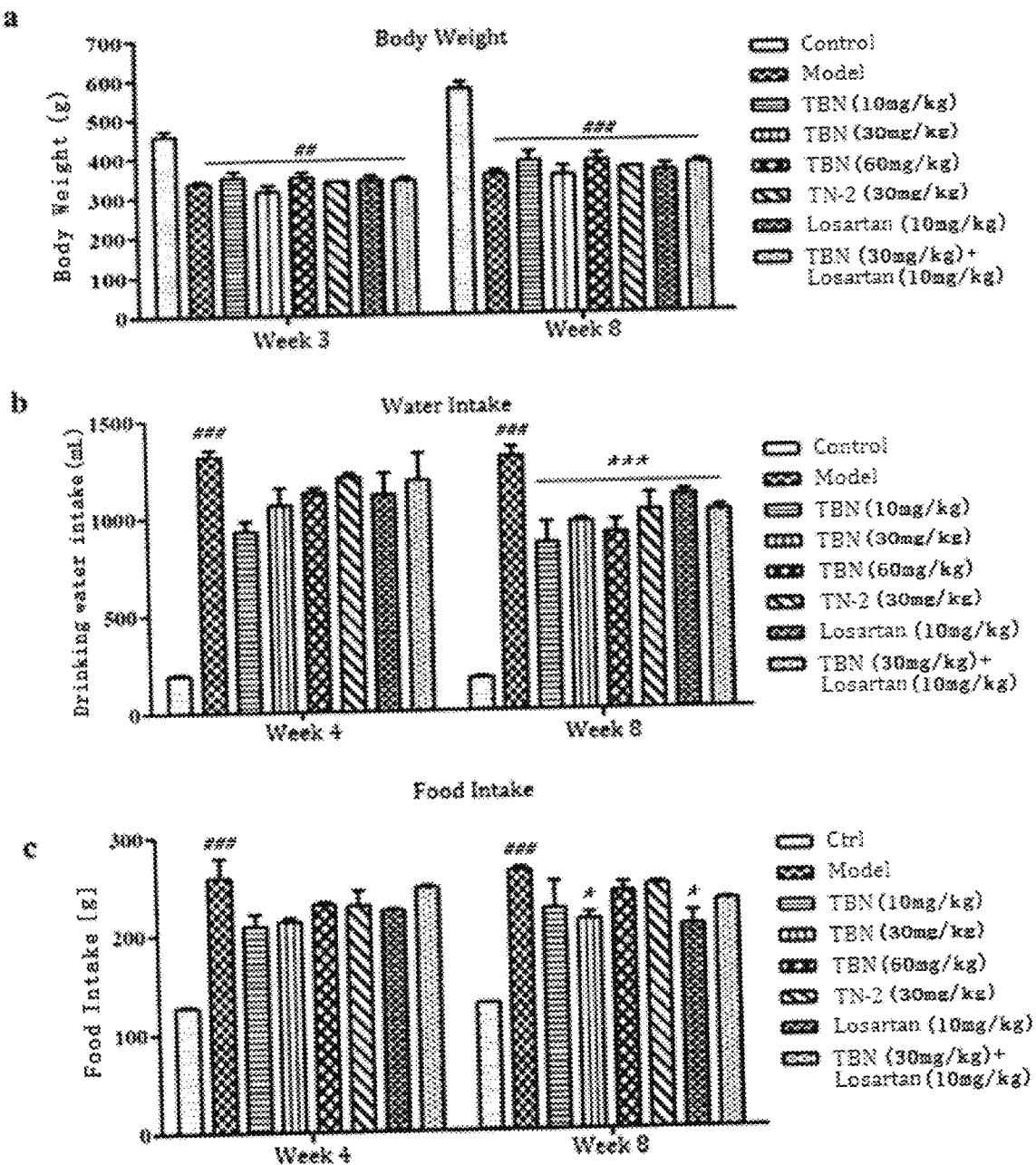
FIG. 1 shows the effect of ligustrazine nitrone derivatives on body weight (FIG. 1a), water intake (FIG. 1b), and food intake (FIG. 1c) of STZ-induced DKD rats. ####$P<0.001$, ###$P<0.01$ compared with the control group (Control); ***$P<0.001$, *$P<0.05$ compared with the model group (Model).

The effect of ligustrazine nitrone derivatives on the body weight of rats with STZ-induced diabetic nephropathy is shown in FIG. 1a. TBN and TN-2 have no effect on the body weight of rats with diabetic nephropathy. The changes of drinking water and feed volume in diabetic nephropathy rats are shown in FIG. 1b and FIG. 1c. The DKD rats in the TBN and TN-2 treatment groups had significantly lower water intake and food intake than the model group, indicating that TBN and TN-2 can slow the progression of diabetic disease in DKD rats, thereby improve the diabetic symptoms of more water and food intake of the DKD rats.

Example 3. Effect of 1 Ligustrazine Nitrone Derivatives on Retinopathy of the STZ-Induced DKD Rats During the experiment, the retinopathy of rats was observed during daily administration, and the dates of retinopathy in different groups of rats were recorded.

Retinopathy is one of the common complications of diabetic nephropathy and has a high correlation with diabetic nephropathy. The effect of ligustrazine nitrone derivatives on STZ-induced retinopathy of DKD rats is shown in Table 1. The number of retinopathy in DKD rats after TBN and TN-2 treatment was reduced, and the time when retinopathy occurred is relatively delayed. The results indicate that the ligustrazine nitrone derivatives TBN and TN-2 can reduce and delay the occurrence of retinopathy.

Example 4. Effect of Ligustrazine Nitrone Derivatives on Blood Glucose and Urine Protein in DKD Rats Induced by STZ During the experiment, the blood glucose of the rats was monitored after the completion of the modeling and after the completion of the administration, and urine protein was collected once at 24 hour.

Figure 2:
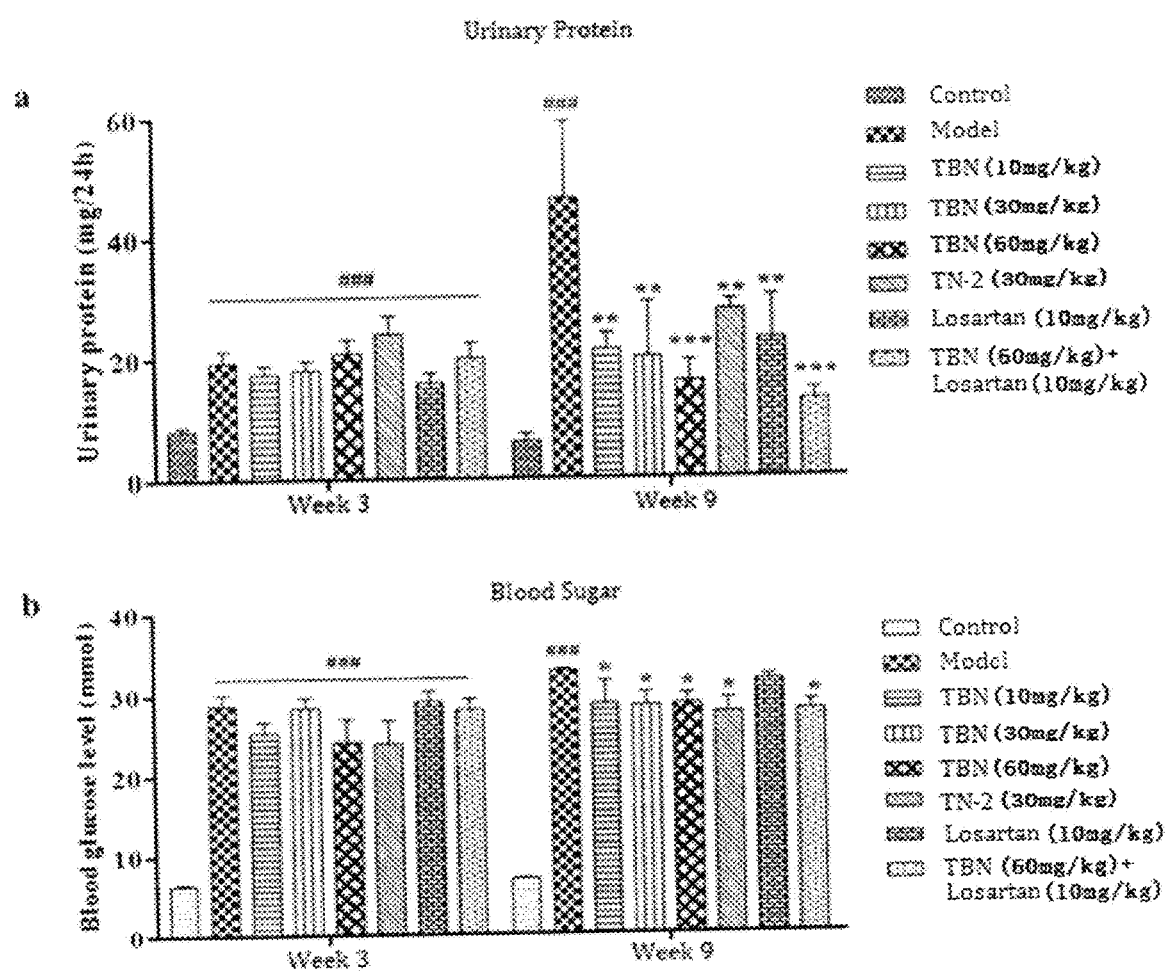
FIG. 2 shows the effect of ligustrazine nitrone derivatives on urinary protein (FIG. 2a) and rat blood glucose (FIG. 2b) of STZ-induced DKD rats. ####$P<0.001$ compared with the control group (Control); $P<0.001$, $P<0.05$, *$P<0.01$ compared with the model group (Model).

The effect of ligustrazine nitrone derivatives on blood glucose of STZ-induced DKD rats is shown in FIG. 2a. The blood glucose was significantly increased after 3 weeks of STZ induction, and was significantly decreased after 6 weeks of treatment with TBN and TN-2. The effect of TBN and TN-2 on urinary protein of STZ-induced DKD rats is shown in FIG. 2b. Urinary protein content in urine of DKD rats treated with TBN and TN-2 was significantly reduced. The combined use of TBN and losartan is superior to treatment with TBN alone or losartan alone.

Example 5. Effect of Ligustrazine Nitrone Derivatives on Serum Biochemical Parameters of STZ-Induced DKD Rats Six weeks after the administration, the rats were anesthetized, and the blood was taken from the abdominal aorta, and, after standing for 1 hour, was centrifuged at 3000 rmp for 10 min and stored at −70° C. Serum levels of creatinine, urea nitrogen, cholesterol and triglycerides were measured using an automated biochemical analyzer.

Figure 3:
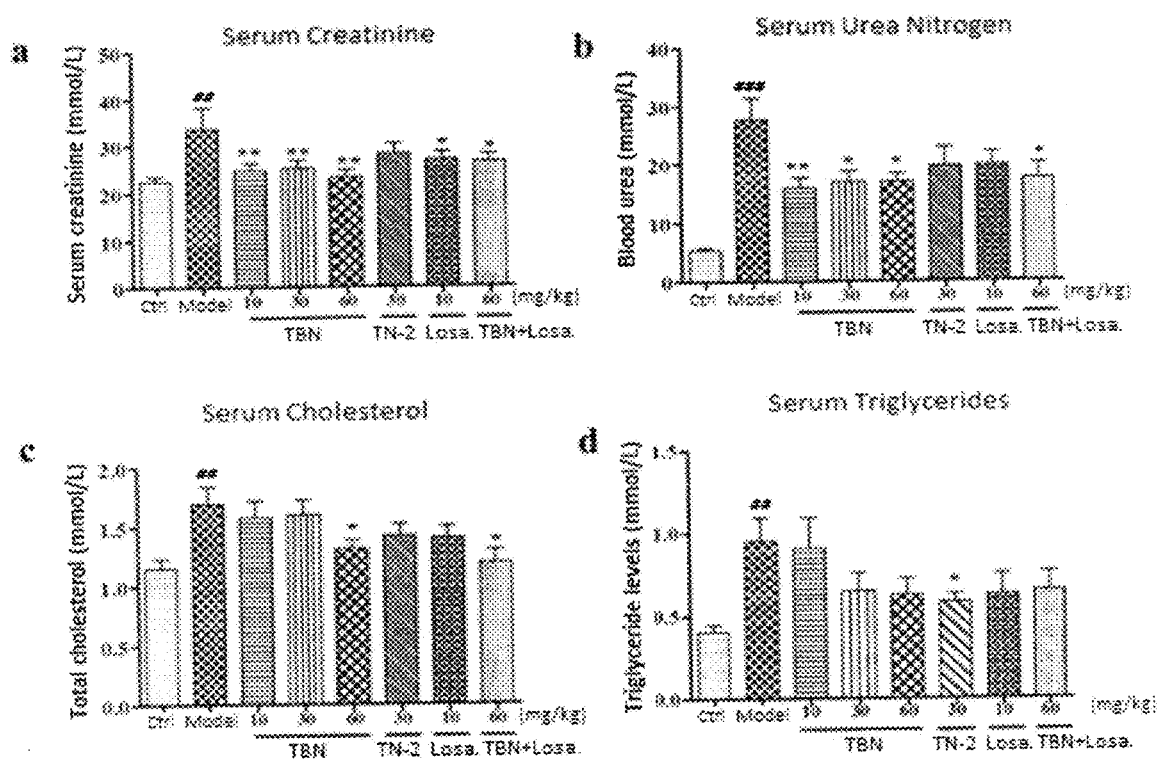
FIG. 3 shows the effect of ligustrazine nitrone derivatives on the levels of serum creatinine (FIG. 3a), urea nitrogen (FIG. 3b), cholesterol (FIG. 3c) and triglycerides (FIG. 3d) in STZ-induced DKD rats. ####$P<0.001$, ###$P<0.01$ compared with the control group (Control); **$P<0.05$, *$P<0.01$ compared with the model group (Model).

Serum creatinine, urea nitrogen, cholesterol and triglyceride levels may reflect the body's lipid metabolism, carbohydrate metabolism and kidney function. The effect of ligustrazine nitrone derivatives on serum creatinine, urea nitrogen, cholesterol and triglycerides in STZ-induced DKD rats is shown in FIG. 3. TBN and TN-2 can significantly reduce serum creatinine (FIG. 3*a*), urea nitrogen (FIG. 3*b*), cholesterol (FIG. 3*c*) and triglyceride (FIG. 3*d*) levels, in a dose-dependent manner, showing improvement in lipid metabolism, carbohydrate metabolism and renal function in STZ-induced diabetic nephropathy rats.

Example 6. Effect of Ligustrazine Nitrone Derivatives on Kidney Index of STZ-Induced DKD Rats After 6 weeks of administration, the kidney tissue was uniformly separated by an autoclave surgical instrument, and washed with normal saline. After the filter paper was blotted, the fine balance was weighed, and then stored in a refrigerator at −80° C. for use. Kidney index (relative to kidney weight) is kidney weight (mg)/body weight (g)=BW/KW.

Figure 4:
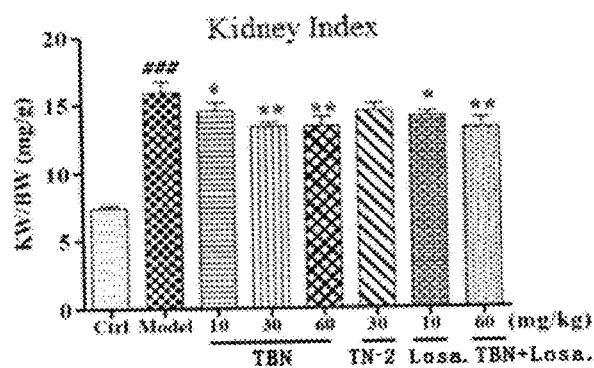
FIG. 4 shows the effect of ligustrazine nitrone derivatives on kidney index in STZ-induced DKD rats. ####$P<0.001$ compared with the control group (Control); **$P<0.05$, *$P<0.01$ compared with the model group (Model).

With the progress of pathological process of diabetic nephropathy, the glomerular basement membrane gradually thickens, the mesangium further widens, and focal tubular atrophy and interstitial fibrosis were finally developed with renal failure. The kidney index responds to, in certain extent, the pathological condition of diabetic nephropathy. The effect of ligustrazine nitrone derivatives on kidney index in STZ-induced DKD rats is shown in FIG. 4, TBN and TN-2 significantly reduced the kidney index of DKD rats, indicating that TBN and TN-2 can delay the progression of diabetic nephropathy.

Example 7. Effect of Ligustrazine Derivatives on Rats with Diabetes with Neuropathy Modeling method: STZ was weighed and transferred to a centrifuge tube, wrapped with aluminum foil, kept away from light, and stored at −20° C. STZ sodium citrate solution is prepared when it is in need to use. The rats were fasted without water for 12 hours before injection. After weighing, the rats were injected with 55 mg/kg STZ intraperitoneally (STZ needs to be injected quickly, and the injection was completed within 10 minutes), and then returned to the cage to ensure that the rats had sufficient drinking water for 24 hours. Rats were injected with an equal volume of citrate buffer (pH 4.5). Four weeks after STZ injection, blood was collected from the tail vein, and the rats with blood glucose less than 16.7 mmol/L were eliminated; the taillick threshold temperature was increased, and the mechanical withdrawal threshold (MWT) was decreased, as the standard of a successful DPN model.

The animals were randomly divided into 3 groups (n=7), namely the normal control group, the model group, and the TBN (30 mg/kg) group. The normal group and the model group were injected with an equal volume of normal saline, and TBN was administered twice a day (fixed at 9:00-10:00 am and 3:00-4:00 pm), continuously for 4 weeks.

Experiment for detecting mechanical pain threshold: In a quiet environment, the rats were individually placed in a porous steel wire cage. After adapted to the environment for 15 minutes, the rats were treated by using an electronic von Frey stimulating needle to stimulate the middle of the hind limbs, with the intensity being gradually increased from small to large. When the rats have a withdrawal reaction, the pressure value displayed on the von Frey electronic recorder was recorded. Each of the rats was stimulated 3 times with an interval greater than 30 s, and the average value was taken as the mechanical pain threshold of the rat.

Experimental results are shown in FIG. 6. The administration was started 4 weeks after STZ injection, and the mechanical withdrawal threshold of the hind limbs of the rats was measured after 2 weeks and 4 weeks of administration. Experimental results indicated that, compared with the blank control group, the pain threshold of mechanical stimulation in the model group was significantly reduced after 6 weeks of STZ injection (i.e., 2 weeks after administration) ($P<0.05$); the pain threshold of mechanical stimulation in TBN administration group was similar to that of the model, with no statistically significant difference between the two groups. Eight weeks after STZ injection (i.e., 4 weeks after administration), the mechanical pain threshold of the model group decreased significantly, which was significantly different from that of the blank control group ($P<0.05$); TBN treatment group increased the mechanical pain in the middle of the hind foot of diabetic rats, wherein the pain threshold of stimulation was significantly different from the model group ($P<0.05$).

Thermal radiation stimulation experiment: 2 weeks and 3 weeks after STZ injection, observation was made on whether the rats have hyperalgesic behaviors with thermal temperature. At room temperature ($24\pm1°$ C.), the rat was placed in a transparent plastic observation box with a heat radiation source at the bottom. When the thermal stimulation started, a timer was started to record the latency of the rat's hind limbs. Each rat was performed 3 thermal radiation experiments with an interval of 5 minutes, and the stimulation time of each thermal radiation was 30 seconds.

The experimental results are shown in FIG. 7. After 4 weeks (prior to the administration), 6 weeks (administration for 2 weeks) and 8 weeks (administration for 4 weeks) of STZ injection, heat radiation stimulation experiment was respectively performed, and the rat's hindlimb lifting latency was observed and recorded. The experimental results indicated that compared with the blank control group, the thermal stimulation pain threshold of the model group was significantly reduced 4 weeks after STZ injection (i.e., before administration) ($P<0.05$); the TBN administration group had no statistical significant difference compared with the model group. Six weeks after STZ injection (i.e., 2 weeks after administration), the thermal stimulation pain threshold of the model group further decreased, which was significantly different from that of the blank control group ($P<0.001$). After 8 weeks of STZ injection (i.e., 4 weeks of administration), the TBN treatment group can increase the pain threshold of heat stimulation in the middle of the hind foot of diabetic rats, which has a statistically significant difference compared with the model group ($P<0.05$).

The above experiments show that diabetic rats have hyperalgesia, and TBN can effectively relieve pain and increase the threshold of pain tolerance.

Example 8. Tests on Cell Hypoxia Model

Establishment of Cell Hypoxia Model

HepG2 cell cryopreservation tube was thaw in a 37° C. water bath, and 3-4 times volume of the cell suspension of the complete medium was added and mixed well, and centrifuged at 1000 r/min for 5 min, the supernatant was discarded and then transferred to a culture flask. To the culture flask was added 5 ml of complete medium (10% FBS+90% DMEM), and the flask was placed in a 37° C., 5% $CO_2$ cell incubator overnight. When the density of HepG2 cells in the culture flask reaches 80%, the culture medium was discarded, and washed twice with 2-3 mL HBSS buffer to completely remove the serum-containing medium. To the culture flask was added 1 mL of 0.25% pancreatin-0.02% EDTA and the culture flask was placed in a 37° C. incubator for digestion for about 2 minutes. The culture flask was taken out and the cell morphology was observed under the microscope to obtain small round cells. The 0.25% pancreatin-0.02% EDTA was discarded, 3 mL complete medium was added for washing, the cells on the wall of the culture flask were blown, and the blew down cell suspension was transferred to a new culture flask for culture, the ratio of each passage is one to three. After the cells have been passaged for 2-3 times, a 50 µM of the hypoxia modeling agent cobalt chloride ($CoCl_2$) was used for modeling. Inoculation was carried out in a six-well plate at a density of 80,000 cells/ml, with 1.5 mL per well, three groups (control, $CoCl_2$, TBN30), for 24 h until the cells adhere to the wall. After the cells adhered, the medium of the $CoCl_2$ and TBN 30 groups was changed to 50 µM $CoCl_2$— pure medium, and the control group was changed to pure medium, and the cells were cultured for 24 hours to construct the hypoxia model of cells. After 24 hours of incubation, the original medium was discarded, the control group was added to the drug-free pure medium (DMEM), the model group was added to 50 µM $CoCl_2$-pure medium, and the drug group was added to 50 µM $CoCl_2$ containing 30 µM TBN-pure culture medium, for continuing cultivation for 24 h.

Detection of Cellular EPO Level by RT-PCR

A (buffer RZ) lysis solution was added to the culture plate to lyse the cells, with 1 mL of RZ added per 10 $cm^2$ area, and slapped several times with a sampler until the solution is transparent. The homogenized sample was placed at 15-30° C. for 5 minutes to completely separate the nucleic acid-protein complexes. 200 µL of chloroform was added, the tube was covered, shake vigorously for 15 sec, and left at room temperature for 3 min. After centrifuged at 4° C. and 12,000 rpm for 10 min, the sample was separated into a yellow organic phase, an intermediate layer and a colorless water phase. The RNA is mainly in the water phase, and the volume of the water phase is about 50% of the RZ reagent used in the lysis solution. The water phase was transferred to a new tube, slowly added with 0.5 times the volume of absolute ethanol, mixed well. The obtained solution and the precipitate were transferred to an adsorption column CR3, and centrifuged at 4° C. and 12,000 rpm for 30 sec. A 500 µL of protein-removing solution RD was added to the adsorption column CR3 and centrifuged for 30 sec at 4° C. at 12,000 rpm, with the waste liquid being discarded, and the CR3 was placed into a collection tube. A 500 µL of rinsing solution RW was added to the adsorption column CR3, allowed to stand at room temperature for 2 minutes, and centrifuged for 30 sec under the above conditions, and then the waste liquid was discarded. The adsorption column was placed into a 2 ml collection tube and centrifuged for 2 min under the above conditions to remove residual liquid. Finally, the adsorption column CR3 was transferred to a new 1.5 ml centrifuge tube, added with 30-100 µL RNase-Free $ddH_2O$, allowed to stand at room temperature for 2 minutes, and the centrifuged for 2 minutes under the above conditions.

Reverse Transcription to cDNA

FastKing one-step method was used to remove genomic cDNA first-strand synthesis premix reagent to prepare first-strand cDNA. 50 ng-2 µg total RNA can establish a 20 µL reaction system.

1. The template RNA was thawed on ice; 5× FastKing-RT SuperMix and RNase-Free $ddH_2O$ were thawed at room temperature (15-25° C.), and immediately placed on ice after thawing. Each solution was vortexed to mix well before use, and centrifuged briefly to collect the remaining liquid on the tube wall.

The following steps are performed on ice. In order to ensure the accuracy of the preparation of the reaction solution, during the preparation of the reaction system, a Mix should be prepared first, and then dispensed into each reaction tube, respectively.

Establishment of Total RNA Reaction System

The reverse transcription reaction system was prepared as shown in Table 2 below.

TABLE 2

Reverse transcription reaction system

| Component | Amount of use |
| --- | --- |
| 5× FastKing-RT SuperMix | 4 µL |
| Total RNA | 50 ng-2 µg |
| RNase-Free $ddH_2O$ | Up to 20 µL |

The reverse transcription reaction was performed as shown in Table 3 below.

TABLE 3

Parameters of reverse transcription reaction

| Reaction temp. | Reaction time | Notes |
| --- | --- | --- |
| 42° C. | 15 min | Removal of genome and reverse transcription reaction |
| 95° C. | 3 min | Enzyme inactivation process |

Quantification of cDNA Amplification

1. A 0.2 ml PCR tube was taken to prepare the following reaction system, with 3 tubes for each reverse transcription product.

| 2× qPCR Mix | 10 µL |
| --- | --- |
| Gene primer | 2.0 µL (F/R) |
| Product of reverse transcription | 1 µL |
| $ddH_2O$ | 5.0 µL |

For the primers, see Jussi-Pekka Tolonen. et al., A long hypoxia-inducible factor 3 isoform 2 is a transcription activator that regulates erythropoietin, Cellular and Molecular Life Sciences (2020) 77: 3627-3642).

2. PCR amplification

| Pre-denaturation | 95° C., 10 min |
| --- | --- |
| Cycle (40 times) | 95° C., 15 s→60° C., 60 s |
| Melting curve | 60° C.→95° C., heating up 0.3° C. every 15 sec. |

The expression result of EPO mRNA level in the HepG2 cell hypoxia model is shown in FIG. 8. TBN30 can significantly increase the expression of EPO mRNA in the HepG2 cell hypoxia model induced by cobalt dichloride. Experiments indicate that TN-2 can also increase the expression of EPO mRNA in cells in the hypoxia model caused by cobalt dichloride.

Example 9. Making and Grouping of Rat Model of STZ-Induced Diabetic Nephropathy (1) Establishment of SD Rat DKD Model Induced by STZ Before the injection, the rats were fasted for 12 hours without water. After weighing, the rats were injected with 55 mg/kg STZ intraperitoneally (STZ needs to be injected quickly, and the injection was completed within 10 minutes), and then returned to the cage to ensure that the rats had sufficient drinking water for 24 hours. Rats were injected with an equal volume of citrate buffer (pH 4.5). After STZ injection for 3 weeks, blood was collected from the tail vein, and blood glucose ≥16.7 mmol/L was used as the criteria for the standard of the rats.

(2) Animal Grouping and Administration

After grouping according to the random number table, the specific conditions of each group of rats are shown in Table 4 below:

TABLE 4

Parameters of administration of STZ-induced diabetic nephropathy in rats

| Group | Dosage | Mode of administration | Dosing frequency |
| --- | --- | --- | --- |
| Normal control group (Ctrl) | / | i.g. | twice/day |
| Model group (Vehicle) | / | i.g. | twice/day |
| TBN | 10 mg/kg | i.g. | twice/day |
| TBN | 30 mg/kg | i.g. | twice/day |
| TBN | 60 mg/kg | i.g. | twice/day |
| Losartan | 10 mg/kg | i.g. | once/day |

The route of administration is intragastric administration. TBN was administered twice a day (fixed at 9:00-10:00 am and 3:00-4:00 pm), and Losartan was administered once a day (fixed at 9:00-10:00 am) continuously for 6 weeks.

Effect of TBN on the Morphology of Kidney Tissue in DKD Rats Induced by STZ

Figure 9:
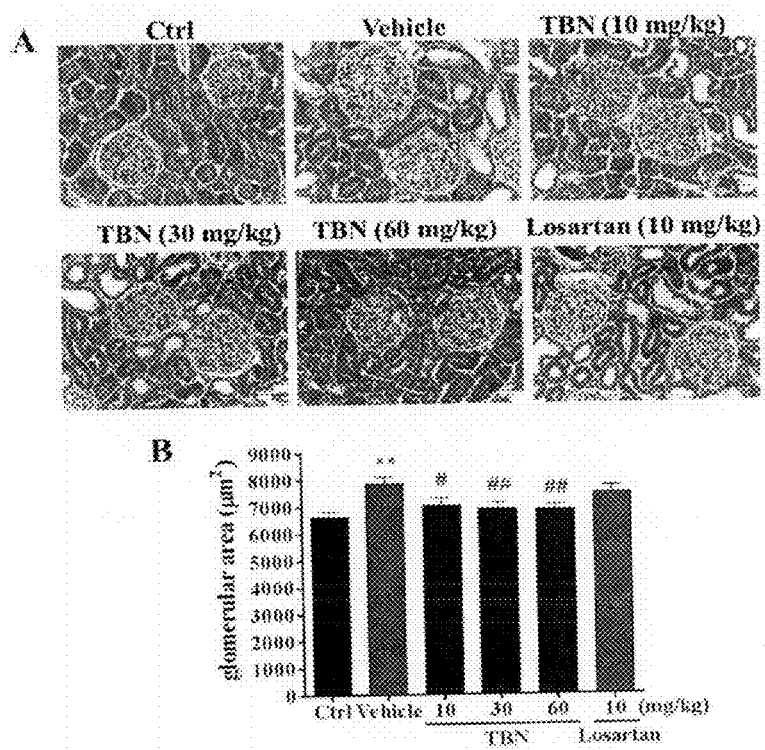
FIG. 9 shows the effect of TBN on the kidney morphology of DKD rats induced by STZ. **$P<0.01$ compared with the control group (Control); #$P<0.05$, ##$P<0.01$ compared with the model group (Model). Wherein, control group: n=16; model group: n=13; TBN 10 mg/kg group: n=16; TBN 30 mg/kg group: n=16; TBN 60 mg/kg group: n=16; Losartan 10 mg/kg group: n=16.

At the end of the experiment, kidney tissues were quickly separated, fixed with 4% paraformaldehyde and embedded in paraffin, serially sliced, 5 μm each, dried at 37° C. for 1 h, and then stained with hematoxylin and eosin (HE). The process is briefly as follows: paraffin sections were taken out of the 65° C. oven and immediately put in xylene to dewax and rehydrated with gradient alcohol, stained with hematoxylin staining solution for 10 minutes, and microscopically controlled alcohol differentiation with 1% hydrochloric acid was performed until the chromatin of the nucleus and the nucleus becomes clear; 1% ammonia water-ethanol solution is blue; 0.5% eosin Y-ethanol solution is stained for 3 min, and finally dehydrated routinely, mounted, and the tissue morphology changes are observed under a light microscope. The staining results indicated that the glomerulus and renal tubules in the Ctrl group were clear and regular, the renal tubular epithelial cells were neatly arranged and there was no abnormality, there was no thickening of capillary basement membrane, mesangial cells and extracellular matrix proliferation, and no mesangial area, no apparent inflammatory cell infiltration, no glomerular exudation and adhesion. The glomerular volume of rats in the DKD group of the Vehicle group increased, the mesangial area was diffusely widened, the mesangial cells were proliferated, the capillary loops were expanded, the mesangial matrix increased, and the glomerular capillary basement membrane was irregularly thickened. Renal pathological changes such as vacuole deformation, shedding of renal tubular epithelial cells and infiltration of a large number of inflammatory cells (FIG. 9A). The statistical results of glomerular area indicated that the glomerular area of rats in the DKD group of the Vehicle group was significantly larger than that of the Ctrl group (P<0.01). The above-mentioned pathological changes were improved in each dose group of TBN, among which 60 mg/kg TBN improved the most. The positive control drug Losartan also improved renal tissue damage, but did not significantly reduce the glomerular area (FIG. 9B).

Figure 10:
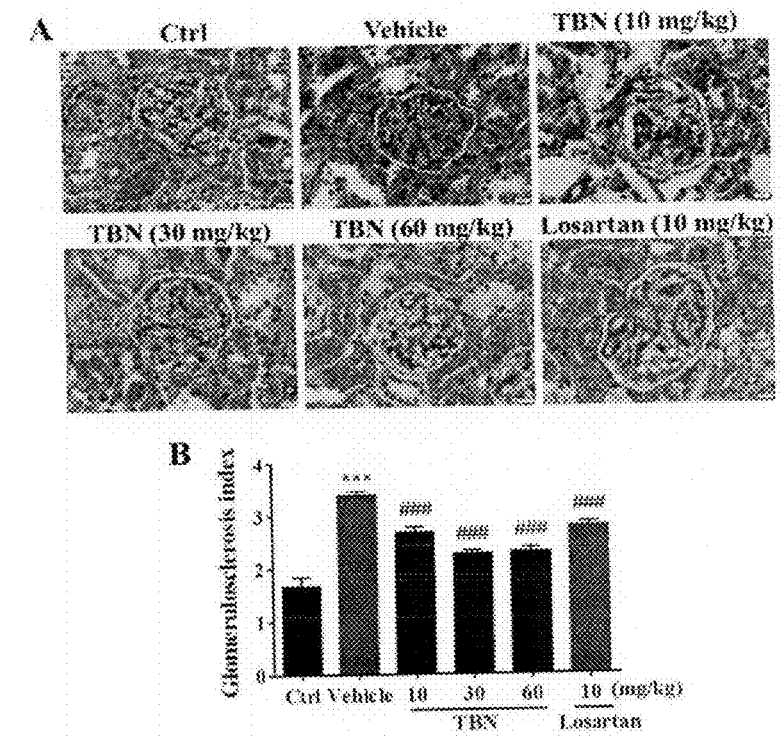
FIG. 10 shows that TBN reduces the glomerulosclerosis index in DKD rats. ***$P<0.001$ compared with the control group (Control); ###$P<0.001$ compared with the model group (Model). Wherein, control group: n=7; model group: n=5; TBN 10 mg/kg group: n=6; TBN 30 mg/kg group: n=6; TBN 60 mg/kg group: n=7; Losartan 10 mg/kg group: n=6.

TBN Significantly Improves the Degree of Glomerular Sclerosis in DKD Rats Induced by STZ At the end of the experiment, kidney tissues were quickly separated, fixed with 4% paraformaldehyde and embedded in paraffin, serially sliced, 5 μm each, dried at 37° C. for 1 h, and then stained with PAS. The process is briefly as follows: paraffin sections are taken out of the 65° C. oven and immediately placed in xylene for deparaffinization and gradient alcohol rehydration, followed by periodic acid treatment for 5 min and Schiff treatment for 10 min, and then differentiation is performed with differentiation solution for 10 s. After rinsing with running water, it returns to blue, and finally dehydration is performed routinely, and the film is mounted. The PAS staining results indicated that the glomerular basement membrane area of rats in the Ctrl group did not change significantly, and the glomerular basement membrane area of rats in the Vehicle group was significantly larger than that in the Ctrl group (FIG. 10A). The glomerular sclerosis index of rats in the Vehicle group was significantly increased, which was significantly different from that in the Ctrl group (P<0.001, FIG. 10B). All doses of TBN and the positive control drug Losartan treatment group can significantly reduce the glomerular sclerosis index of DKD rats (P<0.001, FIG. 10B).

Effect of TBN on the Degree of Interstitial Fibrosis in the Rats of Each Group

Figure 11:
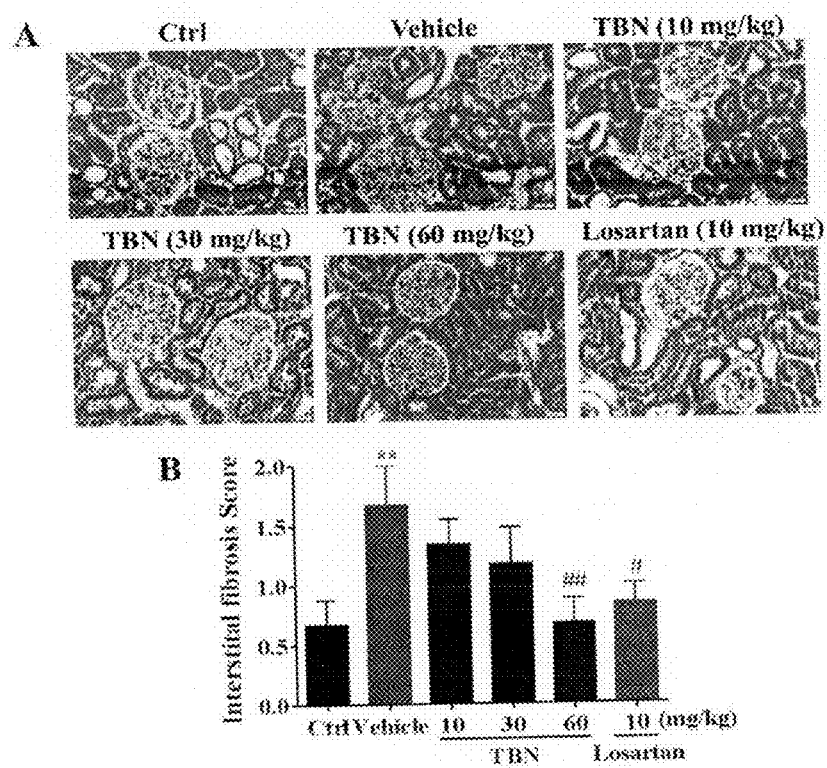
FIG. 11 shows that TBN significantly reduces the interstitial fibrosis index of DKD rats. **$P<0.01$ compared with the control group (Control); #$P<0.05$, ##$P<0.01$ compared with the model group (Model). Wherein, control group: n=6; model group: n=6; TBN 10 mg/kg group: n=6; TBN 30 mg/kg group: n=6; TBN 60 mg/kg group: n=6; Losartan 10 mg/kg group: n=6.

At the end of the experiment, the kidney tissues were quickly separated, fixed with 4% paraformaldehyde and embedded in paraffin, serially sliced, 5 μm each, dried at 37° C. for 1 h, and then subjected to Masson staining. The process is briefly as follows: paraffin sections are taken out of the 65° C. oven and immediately put in xylene for dewaxing and gradient alcohol rehydration, according to the kit instructions, add reagent A (a mixture of equal amounts of A1 and A2) for dyeing for 8 min; then use Reagent B differentiates and reagent C turns blue; reagent D stains for 7 min; reagent E washes for 1 min; reagent F washes for 1 min; reagent G stains for 1 min; dehydrated with 95% ethanol and absolute ethanol, transparent xylene, sealed with neutral gum piece. The staining results indicated that compared with rats in the Ctrl group, the area of glomerular and tubular interstitial fibrosis in the Vehicle group was significantly larger than that in the Ctrl group (FIG. 11A). The interstitial fibrosis index of rats in the Vehicle group increased significantly, which was significantly different from that of the Ctrl group (P<0.01, FIG. 11B). TBN treatment groups decreased the interstitial fibrosis index in a dose-dependent manner, and 60 mg/kg TBN improved the most significantly (P<0.01). The positive control drug Losartan group also significantly reduced the interstitial fibrosis index compared with the vehicle group rats (P<0.05, FIG. 11B).

Effect of TBN on the Serum Iron Content of STZ-Induced DKD Rats

Figure 12:
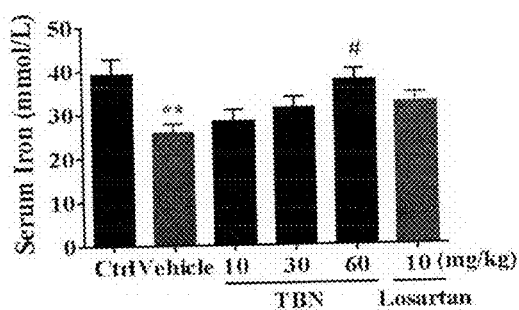
FIG. 12 shows that TBN increases the iron content in the serum of STZ-induced DKD rats. **$P<0.01$ compared with the control group (Control); #$P<0.05$ compared with the model group (Model). Wherein, control group: n=15; model group: n=13; TBN 10 mg/kg group: n=16; TBN 30 mg/kg group: n=16; TBN 60 mg/kg group: n=16; Losartan 10 mg/kg group: n=16.

At the end of the experiment, after rats were anesthetized, blood was taken from the abdominal aorta. After standing for 1 hour, the rats were centrifuged at 3000 rpm for 10 minutes and stored in aliquots at −80° C. An automatic biochemical analyzer was used to detect the content of iron ions in the serum. The experimental results are shown in FIG. 12. The serum iron content of rats in the Vehicle group was significantly reduced compared with the Ctrl group (P<0.01); each administration group of TBN increased the serum iron content in a dose-dependent manner, especially when TBN was high. The increase in the dose group was the most significant, and the increase in serum iron content was statistically different from that in the Vehicle group (P<0.05).

Effect of TBN on Serum Erythropoietin in STZ-Induced DKD Rats

Figure 13:
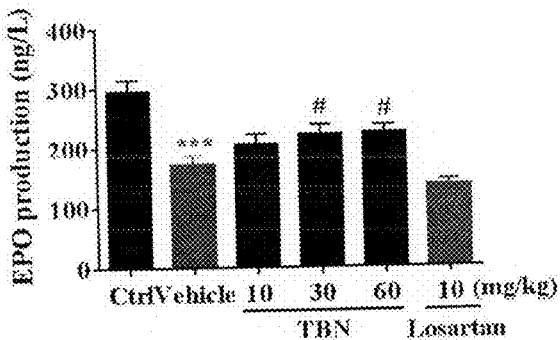
FIG. 13 shows that TBN increases the EPO content in the serum of STZ-induced DKD rats. ***$P<0.001$ compared with the control group (Control); #$P<0.05$ compared with the model group (Model). Wherein, control group: n=15; model group: n=13; TBN 10 mg/kg group: n=16; TBN 30 mg/kg group: n=16; TBN 60 mg/kg group: n=16; Losartan 10 mg/kg group: n=16.

At the end of the experiment, after rats were anesthetized, blood was taken from the abdominal aorta, allowed to stand for 1 hour, the supernatant was collected by centrifugation at 3000 rmp for 10 min. The serum erythropoietin level was measured according to the kit operating instructions. The process is briefly described as follows: Take the ELISA plate to equilibrate to room temperature, prepare the standard product according to the ratio dilution method, set the blank hole, the standard product hole and the sample hole to be tested, the blank control hole does not add the sample, only add the color developer A and B and quenching solution for zero adjustment; standard well: add 50 μL of diluted standard, 50 μL of standard/sample diluent for 0 ng/L group; add 50 μL of sample to test sample well; add biological for all groups 50 μL of antigen working solution, cover with the sealing membrane, gently shake and mix, incubate in a 37° C. incubator for 60 min, carefully remove the sealing membrane, discard the liquid, spin dry, fill each well with washing solution, and discarded after standing for 30 s, repeated 5 times. After exhausting the remaining liquid in the wells, add 50 μL of developer A and 50 μL of developer B to each well, shake gently to mix, and develop color at 37° C. in the dark For 10 minutes, add 50 μL quenching solution to each well to stop the reaction. In the measurement, the blank hole was adjusted to zero, and the absorbance (OD value) of each hole was measured in sequence with a wavelength of 450 nm. Calculate the linear regression equation of the standard curve according to the concentration and OD value, and then calculate the corresponding sample concentration on the regression equation according to the OD value of the sample. The experimental results are shown in FIG. 13. The serum EPO content in the vehicle group was significantly reduced compared to the Ctrl group (P<0.001); compared to the vehicle group, the TBN dose groups increased the serum EPO content to varying degrees. The content of 30 mg/kg and 60 mg/kg TBN increased EPO content with significant statistical difference (P<0.05).

Example 10. Establishment and Grouping of a Mouse Model of Type 2 Spontaneous Diabetic Nephropathy (1) Establishment of a Mouse Model of Type 2 Spontaneous Diabetic Nephropathy db/db mice are congenital obese type 2 DKD mice with spontaneous mutations in the leptin receptor (Leptin receptor, Lepr) due to a point mutation in the leptin receptor gene GT located on chromosome 4. The course of polyphagia, polyuria, diabetes and hyperglycemia is similar to that of humans, and it is currently the most widely used type 2 spontaneous animal model of DKD. The db/db mice have a series of complications with the aggravation of diabetes. The main pathological changes of renal tissue are the expansion of the glomerular mesangial interstitium, the thickening of the glomerular basement membrane, and the excessive accumulation of extracellular matrix. However, the glomerular mesangium of db/db mice changes relatively slowly, and the glomerular mesangium will not be dissolved or nodular glomerulosclerosis, and there is no progressive renal insufficiency.

(2) Animal Grouping and Administration are Shown in Table 5 Below

TABLE 5

Specific situation of administration in mice with type 2 spontaneous diabetic nephropathy

| Group | Dosage | Mode of administration | Dosing frequency |
|---|---|---|---|
| wt/wt | / | i.g. | twice/day |
| db/db | / | i.g. | twice/day |
| db/db + TBN | 10 mg/kg | i.g. | twice/day |
| db/db + TBN | 30 mg/kg | i.g. | twice/day |
| db/db + TBN | 60 mg/kg | i.g. | twice/day |
| db/db + Losartan | 10 mg/kg | i.g. | once/day |

Six-week-old db/db mice were purchased, and start the administration after adaptive feeding for 1 week (i.e., 7-week-old). TBN is administered twice a day (fixed by starting from 9:00-10:00 am and 3:00-4:00 pm, with an interval of 6 hours), and the positive control drug Losartan was administered once a day (fixed at 9:00-10:00 am) for 6 weeks.

Figure 14:
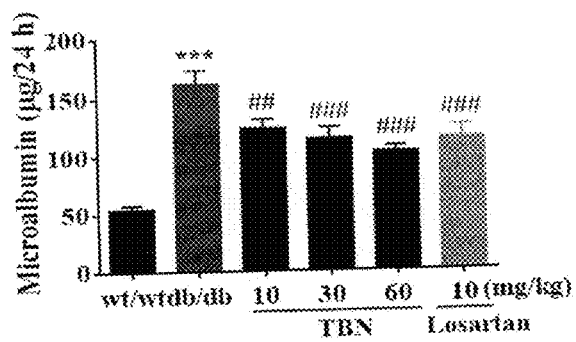
FIG. 14 shows the effect of TBN on 24 h urine microalbumin in db/db mice. ***$P<0.001$ compared with the wild group (wt/wt), ##$P<0.01$, ###$P<0.001$ compared with the model group (db/db). Wherein, wild group: n=10; model group: n=10; TBN 10 mg/kg group: n=10; TBN 30 mg/kg group: n=10; TBN 60 mg/kg group: n=10; Losartan 10 mg/kg group: n=10.

Effect of TBN on 24 h Urine Microalbumin in db/db Mice db/db mice were tested for 24 h urine microalbumin in the 4th and 6th week after drug treatment. The db/db mice of each group were placed in a metabolic cage, free to drink, 24 hours of urine specimens were collected, all urine specimens were preserved with toluene, the urine was centrifuged for 24 h to remove precipitation, placed in a 1.5 mL EP tube, and placed in a −20° C. refrigerator In standby, the ELISA kit detects the content of microalbuminuria. The process is briefly as follows: experimentally set up blank wells, standard wells and sample wells to be tested. In the blank control wells, only chromogenic reagent A&B and quenching solution were added, and no other reagents were added; each well of the standard wells was added with 50 μL of standards of different concentrations and 50 μL of streptomycin-horseradish peroxidase; 40 μL of sample was added to each well to be tested, then 10 μL of microalbuminuria antibody and 50 μL of streptavidin-horseradish peroxidase were added, shaked gently to mix and incubated in a 37° C. incubator for 60 min; then at least 350 μL of washing solution was added, soaked for 30 s and then discarded, repeated for 5 times, after the last washing, the remaining washing solution in the wells was absorbed; 50 μL of developer A and 50 μL of developer B were added to each well, gently shaked and mixed, reacted in a 37° C. incubator in the dark for 10 minutes; finally, 50 μL quenching solution was added to each well, and as this time, the reaction solution turns from blue to yellow, and the reaction is terminated. The absorbance value (OD value) was measured at 450 nm wavelength; the blank control hole was used for adjusting zero, the microalbuminuria standard concentration was used as the abscissa, the OD value as the ordinate, the standard curve regression equation was calculated, and on the basis of the regression equation and the sample's OD value, the concentration of the sample was determined. The experimental results indicated that the level of urinary microalbumin in db/db mice was significantly increased relative to that in the wt/wt group ($P<0.001$, FIG. 14), which was statistically different ($P<0.001$). At the end of 6 weeks of TBN administration, the TBN administration groups dose-dependently reduced the 24 h urine microalbumin production of db/db mice, especially in the 30 and 60 mg/kg TBN administration groups ($P<0.001$); The positive control drug Losartan also significantly reduced the 24 h urine microalbumin production ($P<0.001$).

Effect of TBN on Pathological Histology of db/db Mice

Figure 15:
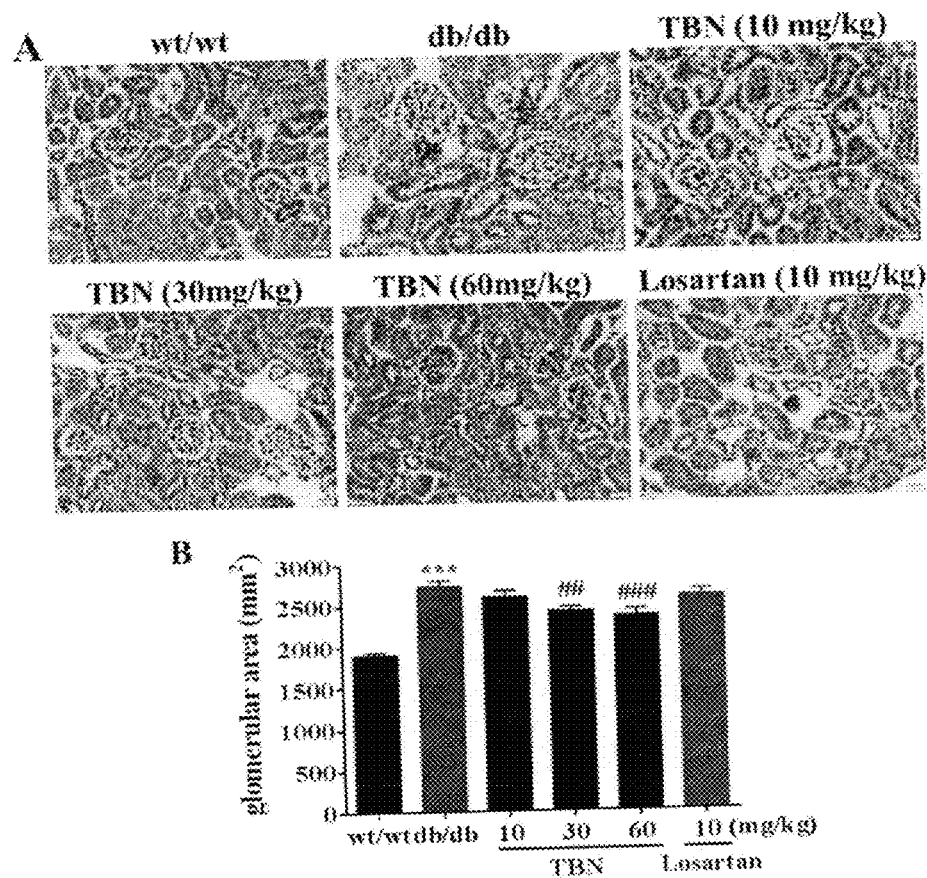
FIG. 15 shows the effect of TBN on the histopathology of kidney tissue in db/db mice. ***$P<0.001$ compared with the wild group (wt/wt), ##$P<0.001$, ###$P<0.001$ compared with the model group (db/db). Wherein, wild group: n=10; model group: n=10; TBN 10 mg/kg group: n=10; TBN 30 mg/kg group: n=10; TBN 60 mg/kg group: n=10; Losartan 10 mg/kg group: n=10.

The HE dyeing process is as shown in Example 9. H&E stain results show that the kidney of the wt/wt group mouse is clear, the capillary distribution is uniform, the renal tubular epithelial cell is arranged intact, and there is no inflammatory cell infiltration, and the glomerular bulb is normal; on the contrary db/db mouse kidney structural disorders, capillary distribution is not even, renal tubular epithelial cell empty bubble is degenerated, renal tubular interstitial cells increases by inflammatory cell infiltration. TBN dose groups showed improvement on the pathological structure of db/db mice injury in various degrees, wherein 30 mg/kg and 60 mg/kg dose groups improve the degree of glomerular structural disorder, and the degree of infiltration of kidney inflammatory cells is obviously improved than the db/db group (FIG. 15A). The glomerular area has increased significantly with respect to wt/wt group ($P<0.001$). TBN treatment groups with dose-dependent show reduced glomerular surface, especially more significantly for TBN 30 mg/kg and 60 mg/kg (FIG. 15B).

Effect of TBN on the Submicroform of db/db Mouse Tissue

Figure 16:
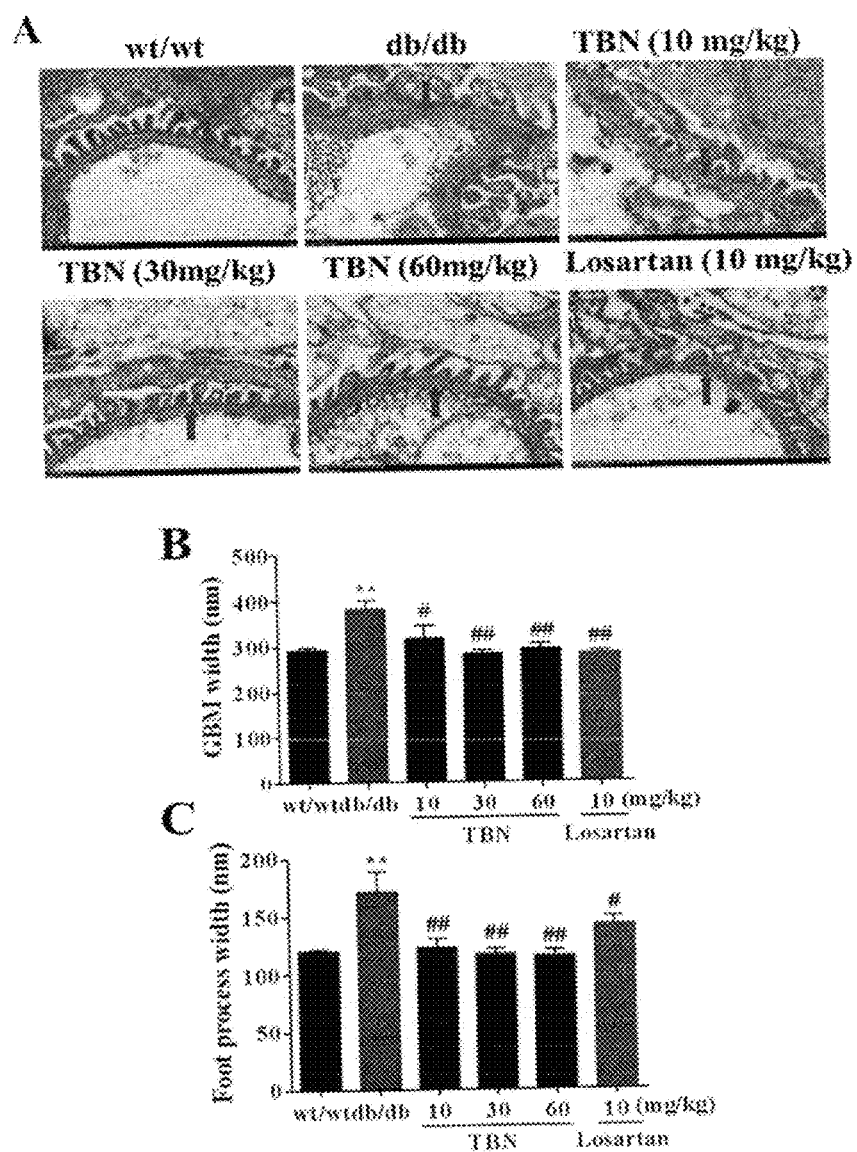
FIG. 16 shows the effect of TBN on the submicroscopic morphology of kidney tissue in db/db mice. **$P<0.01$ compared with the wild group (wt/wt), #$P<0.01$, ##$P<0.01$ compared with the model group (db/db). Wherein, wild group: n=8; model group: n=8; TBN 10 mg/kg group: n=8; TBN 30 mg/kg group: n=8; TBN 60 mg/kg group: n=8; Losartan 10 mg/kg group: n=8.
Figure 17:
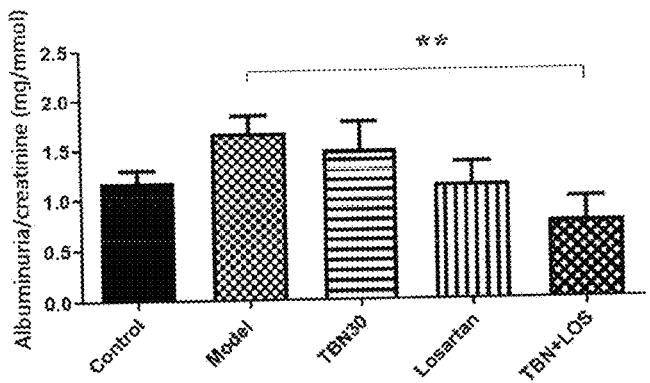
FIG. 17 shows the effect of TBN on urine albumin/creatinine in the urine of db/db mice. Wherein, wild group: n=8; model group: n=8; TBN 30 mg/kg group: n=8; Losartan 10 mg/kg group: n=8; TBN+Losartan group: n=8.

After the mice were executed, the renal cortex was quickly taken with sharp blade (performed on ice); fixed with 2.5% glutaraldehyde (pH 7.4) at 4° C. for 6 h; then fixed for 2 h in a stationary liquid having 1:1 of 0.2 mmol/L PBS and 2% osmic acid, and dehydrated with gradient acetone at 4° C., 10 min for each of 50%, 70%, 90% acetone, then dehydrated with 100% acetone at room temperature twice, each time 15 min; in 1:1 acetone and Epon812 epoxy resin embedded mixed liquid, soaked at room temperature for 30 min; then dipped through the pure furnishings overnight, the embedding agent was made enveloping into tissue blocks completely to replace the dehydrating agent; the samples were embedded in the embedder for ultra-thin slicing, placed at 35° C. for 12 h; placed at 45° C. for 12 h; placed at 60° C. for 48 h; placed in a 37° C. oven for 36 h, in a 60° C. oven for 36 h; 1.5 µm semi-slice was prepared with an ultra-thin slicer; positioning under optical microscope, a trapeter having a top area of about 1 mm² was shaped to prepare 60-70 nm thick ultra-thin slices; dyed in dark with acetate hydroxide liquid for 10 min, and dyed in lead-stained citrate for 10 min. The electron mirror showed the uniform rules of the wt/wt group of glomerular base membranes, the glomerular membrane (GBM, GLOMER bement Membrane) did not appear, the glomerular base film did not appear, renal tubular epithelium. The cells are clearly arranged; in contrast, the db/db group of glomerular base films is significantly thickening, and it is highly fused, and the glomerular measuring membrane is increased, and the dielectric cells are increased (FIG. 16A). TBN (10 mg/kg) group shows slight podocyte fusion, the glomerular membrane has no significant proliferation, and the glomerular base film has a decrease in the Vehicle group ($P<0.05$); TBN (30 mg/kg) group shows podocyte fusion in small area, there was no significant proliferation of the glomerular measuring membrane, relative to the db/db group, and the glomerular base film was significantly reduced ($P<0.01$); TBN (60 mg/kg) group shows no obvious segmental fusion, there was no significant proliferation of glomerular membranes, relative to db/db group, and the glomerular base film was significantly reduced ($P<0.01$). The positive control of Losartan group was well in hemangiectasis, there was no significant increase in the glomerular ferrous matrix, the base film was significantly increased, and the thickness of the glomerular base film was significantly reduced ($P<0.01$).

Effect of TBN on Serum Iron Content of db/db Mice

At the end of the experiment, serum iron content was measured by using automatic biochemical analyzer. The results indicated that the iron content in the serum of the wt/wt group was $40.26\pm7.96$ mmol/L, and the iron content in the serum of the db/db model group was $28.13\pm4.46$ mmol/L, and compared with the wt/wt group, the reduction of ion content is statistically different. After TBN treatment, compared with the db/db model group, the iron content of mice in the TBN 10 mg/kg group was $30.84\pm5.92$ mmol/L, and the iron content of mice in the TBN 30 mg/kg group was $36.20\pm11.89$ mmol/L. The positive control drug Losartan group mouse iron content was $30.62\pm6.73$ mmol/L, and each dose group increased the serum iron content and the effect of increasing iron ions was stronger than the positive control drug group.

Effect of TBN on the EPO Content of the Serum of db/db Mice

At the end of the experiment, after rats were anesthetized, the blood was taken from the abdominal aorta, allowed to stand for 1 h, centrifuged at 3000 rmp for 10 min and with the supernatant collected, and serum erythropoietin levels were measured according to the kit instructions. The process is shown in Example 9, and the results show that, compared with the db/db group, the serum EPO level was slightly lower, the content was $257.19\pm67.80$ ng/L, and the content was 277.24 ng/L for the wt/wt group. After TBN administration, the EPO content of the TBN 10 mg/kg group was $265.04\pm79.32$ ng/kg, the EPO content of the TBN 30 mg/kg group was $288.80\pm36.78$ ng/kg, and the EPO content of the positive control group was $240.70\pm35.68$ ng/kg. In this case, TBN has a tendency to increase the serum EPO level of spontaneous db/db mice, and the above data shows that the increase in serum EPO content in each dose group of TBN is stronger than that of the positive control drug.

Figure 19:
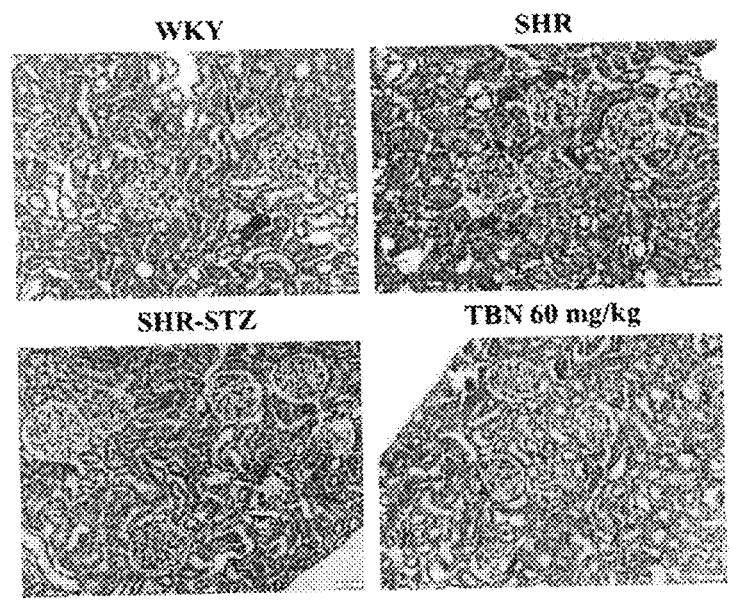
FIG. 19 shows the effect of TBN on the kidney morphology of SHR rats induced by STZ. Wherein, WKY group: n=16; SHR group: n=16; SHR-STZ group: n=16; SHR-STZ+TBN group: n=16; SHR-STZ+Losartan group: n=16.

Example 11. Investigation on the Use of TBN Investigated in Combination with Other Active Substances Grouping and dosing are the same as in Example 9. At the end of the experiment, 24 h urine samples were collected, antiseptic treatment was performed to all urine specimens with toluene, 24 h urine was centrifuged to remove precipitation and placed in a 1.5 mLEP tube and then placed in a refrigerator at −20° C. for later use, urinary albumin content was measured with ELISA kits, urine creatinine levels were detected by use of an automatic biochemical analyzer, and the ratio of both was calculated. The results as shown in FIG. 19 indicate that the ratio of urinary microalbumin to creatinine in DB/DB group was higher than that in wt/wt group, and the db/db mice 24 h urinary albumin creatinine ratio decreased in TBN group, losartan group and TBN-losartan combination group. Referring to this method, metformin (150 mg/kg, qd), and HIF-PH inhibitor roxadustat (10 mg/kg, once 2 every days) were given via oral administration, the combination groups of TBN with respectively metformin and roxadustat also reduce 24 h urinary albumin creatinine ratio.

Example 12. Establishment of Diabetic Model of STZ Induced Spontaneous Hypertensive Rats (1) Establishment of Diabetes Models of STZ-Induced SHR Rats 6 W-age SHR rats were abstained from food but not water for 12 h before injection, and then intraperitoneally injected with 55 mg/kg STZ after weighing (STZ required for fast injection, to be completed within 10 min), then put back to the cage to ensure that rat has sufficient drinking water in the period of 24 h, and the rats of normal control group were injected with citric acid buffer (pH 4.5) in the same volume. After 3 weeks of STZ injection, retinal venous blood was collected, and blood glucose ≥16.7 mmol/L was used as a molding standard, where the model of SHR rats that meet the above criteria is considered successful.

(2) Animal Grouping and Administration

Groups were made in accordance with the random number table, and the specific conditions of each group are shown in Table 6:

TABLE 6

Specific parameters of the administration for STZ-induced spontaneous hypertension rats

| Group | Dosage | Mode of administration | Dosing frequency |
|---|---|---|---|
| WKY Group | / | i.g. | twice/day |
| SHR Group | / | i.g. | twice/day |
| SHR-STZ Group | / | i.g. | twice/day |
| SHR-STZ + TBN Group | 60 mg/kg | i.g. | twice/day |
| SHR-STZ + TBN Group | 10 mg/kg | i.g. | once/day |

The route of administration is intragastrical, TBN is administered twice a day (fixed at 9:00-10:00 am and 3:00-4:00 pm), and Losartan is administered once a day (fixed at 9:00-10:00 am), continuously for 6 weeks.

Figure 18:
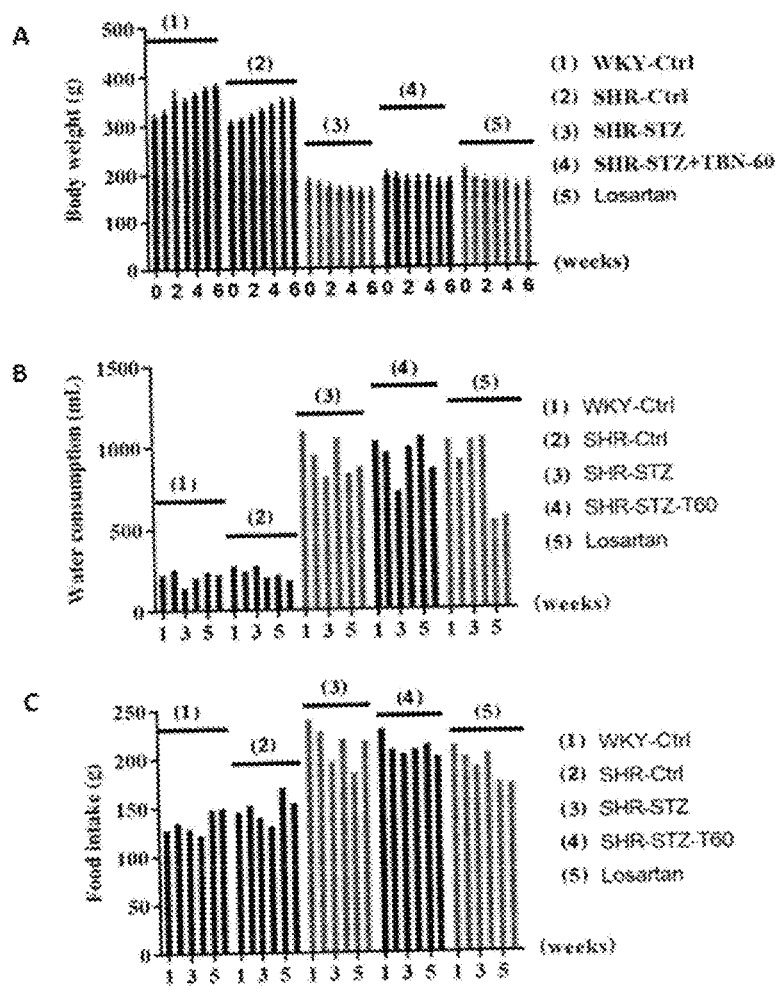
FIG. 18 shows the effect of TBN on the body weight, water intake and diet of STZ-induced SHR rats. Wherein, WKY group: n=16; SHR group: n=16; SHR-STZ group: n=16; SHR-STZ+TBN group: n=16; SHR-STZ+Losartan group: n=16 only.

Effects of Ligustrazine Derivative TBN on the Weight, Food Intake and Water Drinking of the STZ-Induced SHR Rats The general situation and weight changes are observed after the establishment of the rat model, and the general situation includes the activity of rats, mental state, hair color, diet, drinking water and urine volume, etc., and water consumption and feed weights were recorded each week. The STZ-induced SHR rats lost weight, whereas after continuous administration of 6 weeks, the weight of the rats in TBN groups (SHR-STZ-T60 groups), as compared to SHR-STZ group, increased significantly (FIG. 18). After administration of 6 weeks, the total amount of water drinking and food taking in the SHR-STZ group were significantly increased relative to the SHR-Ctrl group (FIG. 18).

Effects of TBN on Morphology of STZ-Induced STR Rats

The process is the same as in Example 9. Dyeing results show that the structure of glomerular and renal tubules of WKY group rats are orderly and clear, neutronized epithelial cells are neatly arranged without any irregularity, and there observed no thinkening of capillary base membrane and hyperplasia of the membrane cells and extracellular matrix, obvious inflammatory cell infiltration, and exudation and adhesion of glomerulose. Tissue slices H&E of SHR-STZ group rats showed visible glomerular bulb volume increase, membraned area diffuse, thin cell hyperplasia, capillary loops expansion, mesangial matrix increase, ghostatic capillary base film irregular thickening, vacuolar deformation and abruption of proximal tubular epithelial cells, and large amounts of inflammatory cell infiltration and other renal pathological changes. To the above pathological changes, use of 60 mg/kg TBN showed improvement (FIG. 21).

Effect of TBN on the Degree of Glomerular Hardening of STZ-Induced SHR Rats

The process is the same as in Example 9. PAS staining results indicated that rats in TBN 60 mg/kg groups were significantly lower than that of the SHR-STZ group ratio (FIG. 20).

Effect of TBN on Serum EPO Content in STZ-Induced SHR Rats

At the end of the experiment, after rats were anesthetized, blood was taken from the rear abdominal aortic pulse, allowed to stand for 1 h, centrifuged at 3000 rmp centrifuged for 10 min to collect supernatant, and the iron ion content was measured by using an automated biochemical device and the level of red cells in serum was detected by using kits. The process is shown in Example 9, and the results indicated that the iron ion content and EPO content in the serum of the SHR-STZ group (Model group) were lower than the SHR group (control) which has statistical significance. Compared to the model group, the TBN group (T60) significantly increased the content of iron ions and EPO in serum (FIG. 21).

Example 13. Rendridic Anemia Model of Ciplatin-Induced C57BL/6J Mice

Modeling method: the animals were randomly divided into 5 groups, i.e., normal control group, model group, three treatment groups, wherein the normal control group was injected with equal volume of normal saline, the model group and three treatment groups were intraperitoneally injected with cisplatin (CDDP) 5 mg/kg once a week, for 4 weeks. Grouping and dosing of the animals are shown in Table 7 below.

TABLE 7

Administration of cisplatin-induced C57BL/6J mice

| Group | Dosage | Mode of administration | Dosing frequency |
|---|---|---|---|
| Normal control group (Ctrl) | / | i.g. | twice/day |
| Model group (model) | / | i.g. | twice/day |
| TBN | 30 mg/kg | i.g. | twice/day |
| TBN | 60 mg/kg | i.g. | twice/day |
| Roxadustat | 10 mg/kg | i.g. | once/two day |

The route of administration is intragastrical. TBN is administered twice a day (fixed at 9:00-10:00 am and 3:00-4:00 pm), and Roxadustat is administered once every two days (fixed at 9:00-10:00 am), for 4 weeks.

Effects of Hepcidin Levels in Mice

Hepcidin is a cysteine-rich antibacterial polypeptide synthesized and secreted by the liver. It plays a negative regulatory role in the regulation of iron balance in the body and can be used to indirectly evaluate the symptoms of anemia in mice. At the end of the administration, compared with the model group, as shown in FIG. 22, the level of iron regulation in model group was significantly increased compared with that in blank control group (P<0.05); compared with model group, TBN 60 mg/kg group significantly reduced the level of iron regulation in renal anemia mice (P<0.05). Roxadustat in positive control group also reduced the level of iron regulation in renal anemia mice, but there was no significant statistical difference. Cisplatin and other chemotherapeutic drugs can cause iron regulation imbalance in mice, and TBN administration can reduce the expression level of iron regulation in the body, and thus can be used to treat cancer complicated renal anemia.

Changes of Erythropoietin in Mice

At the end of the experiment, after rats were anesthetized, the blood was taken from the abdominal aorta, allowed to stand for 1 hour, centrifuged at 3000 rpm for 10 min, and stored in aliquots at −80° C. The content of erythropoietin in the serum was detected by using of a kit. The experimental results are shown in FIG. 23. After the administration, compared with the model group, the TBN treatment groups can increase the expression of erythropoietin to varying degrees. It can be seen from FIG. 23 that different doses of TBN administration groups can increase the content of EPO in mice, and there is a dose dependence, and the efficacy of the high-dose group is stronger than that of the positive control drug, indicating that the compound of the present invention can be used to treat cancer complicated renal anemia.

The invention claimed is:

1. A method of treatment of a disease of diabetic complications, comprising administration of a therapeutically effectively amount of ligustrazine nitrone derivatives or a pharmaceutical composition thereof; the derivatives have a structure of formula (I):

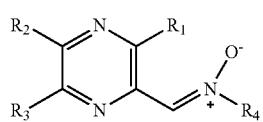

(I)

wherein, $R_1$ and $R_3$ are each independently C1-C6 alkyl; $R_2$ is C1-C6 alkyl or

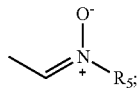

and $R_4$ and $R_5$ are each independently sec-butyl, isobutyl, t-butyl, cyclopentyl or cyclohexyl, wherein the disease of diabetic complications is renal anemia.

2. The method according to claim 1, wherein the C1-C6 alkyl is methyl, ethyl, n-propyl, isopropyl, n-butyl, isobutyl, tert-butyl or n-pentyl.

3. The method according to claim 1, wherein the ligustrazine nitrone derivatives have a structure of formula:

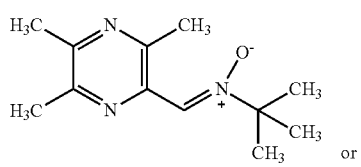

TBN or

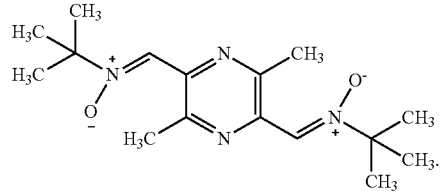

TN-2

4. The method according to claim 1, wherein the renal anemia is caused by decrease in renal erythropoietin production and/or concomitant iron deficiency with renal function declining in course of renal diseases.

5. The method according to claim 1, wherein the renal anemia is diabetic nephropathy renal anemia, chronic kidney disease complicated renal anemia, or cancer complicated renal anemia.

6. The method according to claim 5, wherein the diabetic nephropathy renal anemia is nephropathy renal anemia caused by Type 1 diabetes or Type 2 diabetes.

7. The method according to claim 1, wherein the pharmaceutical composition comprises a therapeutically effective amount of the ligustrazine nitrone derivative or a pharmaceutically acceptable salt thereof, and a pharmaceutically acceptable carrier.

8. The method according to claim 1, wherein the derivatives may be used alone or in combination with other drugs.

9. The method according to claim 8, wherein the other drugs are those used for treatment of diabetes, chronic kidney disease or kidney disease caused by cancer.

10. The method according to claim 8, wherein the other drugs are hypoxia-inducible factor proline hydroxylase (HIF-PH) inhibitors, losartan, metformin, and roxadustat.

11. The method according to claim 8, wherein the other drugs are those used for treatment of diabetes mellitus renal anemia.

12. The method according to claim 8, wherein the other drugs are those used for treatment of hypertension with renal anemia.

13. The method according to claim 8, wherein the other drugs are those used for treatment of diabetes renal anemia.

14. The method according to claim 7, wherein the derivatives can be formulated into various dosage forms with a pharmaceutical carrier, the dosage forms comprising tablets, granules, injections, powders, capsules, and suspensions.

15. The method according to claim 1, wherein the therapeutically effective amount is from 0.001 to 2 g/kg.

16. The method according to claim 9, wherein the other drugs are angiotensin converting enzyme inhibitors, angiotensin II receptor antagonist, calcium channel blockers, beta blockers, diuretics, metformin, sulfonylureas, glinides, alpha glycosidase inhibitor, thiazolidinediones (TZDs), dipeptide peptidase inhibitors, and insulin.

17. The method according to claim 11, wherein the other drugs are biguidine, sulfonylurea, glinides, α-glucosidase inhibitors, thiazolidinediones, dipeptidyl peptidase (DPP-4) inhibitors, and insulin.

18. The method according to claim 12, wherein the other drugs are angiotensin converting enzyme inhibitors, angiotensin II receptor antagonists, calcium channel blockers, β-blockers, and diuretics.

19. The method according to claim 13, wherein the other drugs are biguidine, sulfonylurea, glinides, α-glucosidase inhibitors, thiazolidinediones, dipeptidyl peptidase (DPP-4) inhibitors, and insulin.

* * * * *